United States Patent
Okiyama et al.

(10) Patent No.: US 11,744,773 B2
(45) Date of Patent: Sep. 5, 2023

(54) PUNCTURE NEEDLE CONNECTOR AND CONNECTING TUBE

(71) Applicant: JMS CO., LTD., Hiroshima (JP)

(72) Inventors: Tadashi Okiyama, Hiroshima (JP); Yoshinori Moriyasu, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 1031 days.

(21) Appl. No.: 16/080,934

(22) PCT Filed: Feb. 27, 2017

(86) PCT No.: PCT/JP2017/007278
§ 371 (c)(1),
(2) Date: Aug. 29, 2018

(87) PCT Pub. No.: WO2017/150398
PCT Pub. Date: Sep. 8, 2017

(65) Prior Publication Data
US 2019/0076319 A1    Mar. 14, 2019

(30) Foreign Application Priority Data
Mar. 2, 2016    (JP) ................................. 2016-040110

(51) Int. Cl.
*A61J 1/14* (2023.01)
*A61M 5/162* (2006.01)
(Continued)

(52) U.S. Cl.
CPC ............... *A61J 1/14* (2013.01); *A61M 5/162* (2013.01); *A61M 39/10* (2013.01); *A61M 5/1411* (2013.01); *A61M 39/1011* (2013.01)

(58) Field of Classification Search
CPC .......................... A61M 39/10; A61M 39/1011
See application file for complete search history.

(56) References Cited

U.S. PATENT DOCUMENTS 5,582,600 A * 12/1996 Loh ...................... F16L 37/113
   604/534
6,183,465 B1 * 2/2001 Meier ................... A61M 5/162
   604/905

(Continued)

FOREIGN PATENT DOCUMENTS

JP    2003-214582    7/2003
JP    2004-000483    1/2004
(Continued)

OTHER PUBLICATIONS

Definition of "at", www.merriam-webster.com/dictionary/at.*
(Continued)

*Primary Examiner* — Jessica Arble
(74) *Attorney, Agent, or Firm* — Hamre, Schumann, Mueller & Larson, P.C.

(57) ABSTRACT

A puncture needle connector (1) includes an outer cylinder (11), an inner cavity (1a) formed within the outer cylinder (11), an arm (15) provided at the outer cylinder (11), the arm (15) being elastically deformable by bending, and a claw (16) provided on the arm (15). The inner cavity (1a) is in communication with the outside via a first opening (21) and a second opening (22). When a puncture needle (210) is inserted into the inner cavity (1a) via a first opening (21), the claw (16) engages with an engagement structure (217) provided integrally with the puncture needle (210), a liquid-tight seal (25) is formed between an outer circumferential surface of the puncture needle (210) and an inner circumferential surface of the inner cavity (1a), and the puncture needle (210) and the second opening (22) are in communication with the each other.

12 Claims, 23 Drawing Sheets

(51) Int. Cl.
*A61M 39/10* (2006.01)
*A61M 5/14* (2006.01)

(56) References Cited

U.S. PATENT DOCUMENTS

| | | | | |
|---|---|---|---|---|
| 6,213,996 | B1* | 4/2001 | Jepson | A61J 1/2089 |
| | | | | 604/256 |
| 6,217,564 | B1* | 4/2001 | Peters | A61M 39/1011 |
| | | | | 604/111 |
| 9,079,006 | B1* | 7/2015 | Ovcharchyn | A61M 25/04 |
| 2009/0143758 | A1* | 6/2009 | Okiyama | A61M 39/1011 |
| | | | | 604/408 |
| 2011/0175347 | A1 | 7/2011 | Okiyama | |
| 2011/0178493 | A1 | 7/2011 | Okiyama | |
| 2012/0004644 | A1* | 1/2012 | Strole | A61M 39/26 |
| | | | | 604/540 |
| 2013/0096529 | A1 | 4/2013 | Moradian | |
| 2014/0114292 | A1 | 4/2014 | Tachizaki et al. | |
| 2015/0008664 | A1 | 1/2015 | Tachizaki | |
| 2015/0247597 | A1 | 9/2015 | Okiyama | |
| 2015/0265499 | A1 | 9/2015 | Takeuchi | |
| 2015/0297830 | A1 | 10/2015 | Okiyama | |
| 2016/0067144 | A1* | 3/2016 | Chang | A61M 39/10 |
| | | | | 604/92 |
| 2018/0021512 | A1* | 1/2018 | Fukuoka | A61M 5/1411 |
| | | | | 604/404 |

FOREIGN PATENT DOCUMENTS

| | | |
|---|---|---|
| JP | 2012-254142 | 12/2012 |
| JP | 2013-165830 | 8/2013 |
| JP | 2014-030489 | 2/2014 |
| JP | 2014-079355 | 5/2014 |
| WO | 94/08173 | 4/1994 |
| WO | 2010/061742 | 6/2010 |
| WO | 2010/061743 | 6/2010 |
| WO | 2013/154050 | 10/2013 |

OTHER PUBLICATIONS

Notice of Reasons for Refusal issued in corresponding Japanese Patent Application No. 2016-040110, dated Feb. 25, 2020, 9 pages with translation.

* cited by examiner

PUNCTURE NEEDLE CONNECTOR AND CONNECTING TUBE

TECHNICAL FIELD

The present invention relates to a puncture needle connector that can be connected to a puncture needle with which a rubber stopper is to be pierced. Moreover, the present invention relates to a connecting tube equipped with the puncture needle connector.

BACKGROUND ART

An infusion therapy in which an infusion containing water, nutrition, or the like is administered intravenously to a patient is known. There are cases where a drug is mixed in the infusion in order to treat a disease, for example. In general, an infusion to be administered to a patient is prepared inside an infusion container. After that, one end (upstream end) of an infusion set including a flexible tube is connected to a female connector (port) of the infusion container. A needle at the other end (downstream end) of the infusion set is inserted into a vein of the patient. Then, the infusion in the infusion container is administered to the patient via the infusion set.

Usually, the female connector of the infusion container is provided with a rubber stopper. In order to take out the infusion from the inside of the infusion container via the female connector, it is necessary to pierce the rubber stopper with a puncture needle (also referred to as "spike") having a sharp tip. Therefore, in an infusion therapy, an infusion set with a puncture needle provided at its upstream end may be used.

However, when the rubber stopper is merely pierced with the puncture needle, the puncture needle may unintentionally come off the rubber stopper if tension is applied to the infusion set, for example. In that case, the infusion may leak to the outside.

There are cases where a hazardous drug designated as a powerful drug like some anticancer agents, for example, is mixed in an infusion. In such cases, situations in which the infusion containing the hazardous drug leaks out and adheres to a finger or the like of a worker, or vapor of the leaking infusion is inhaled by the worker must be avoided at any cost.

Thus, it is necessary to prevent unintentional separation of the female connector of the infusion container and the infusion set from each other.

Patent Document 1 discloses an adapter that can be attached to a female connector provided with a rubber stopper. The adapter includes a puncture needle with which the rubber stopper can be pierced and an engaging claw that protrudes toward the puncture needle. When the rubber stopper of the female connector is pierced with the puncture needle of the adapter, the engaging claw engages with the female connector. Thus, even if an external force or vibration is applied, the adapter is prevented from unintentionally detaching from the female connector. The adapter further includes a coinfusion port that is in communication with the puncture needle. The coinfusion port includes a septum (partition wall member) made of an elastic material such as rubber. At the center of the septum, a straight-line shaped slit (cut) penetrating the septum in its thickness direction is formed. The septum functions as a self-closing valve.

Patent Documents 2 to 5 disclose male connectors that can be connected to the coinfusion port of the above-described adapter. Each male connector includes a male luer and a lock claw. In a state in which the male luer is inserted into the slit of the septum, the lock claw can be engaged with the coinfusion port. Thus, even if an external force or vibration is applied, the male connector and the coinfusion port are prevented from unintentionally separating from each other.

A flexible tube can be connected to the male connector so as to be in communication with the male luer. The puncture needle provided at the upstream end of the above-described infusion set can be inserted into an end of the tube that is opposite to the male connector. As a result of inserting the puncture needle into the tube, the diameter of the tube is increased, and the tube is stretched in its circumferential direction. Therefore, the tube and the puncture needle can be connected to each other with relatively high strength.

As described above, it is possible to attach an adapter to a female connector of an infusion container and connect the adapter and a puncture needle of an infusion set to each other via a male connector equipped with a tube.

CITATION LIST

Patent Documents

Patent Document 1: JP 2014-079355A
Patent Document 2: JP 2004-000483A
Patent Document 3: WO 2010/061742
Patent Document 4: WO 2010/061743
Patent Document 5: WO 2013/154050
Patent Document 6: JP 2012-254142A
Patent Document 7: JP 2013-165830A

DISCLOSURE OF INVENTION

Problem to be Solved by the Invention

However, when a puncture needle of an infusion set is merely inserted into a tube, it is difficult to judge whether or not the insertion depth of the puncture needle into the tube is sufficient. If the insertion depth is insufficient, the puncture needle may come off the tube when unintentional tension is applied, for example, and the infusion may leak to the outside. In the case where the infusion contains a hazardous drug, a serious accident in which the worker is exposed to the infusion may occur.

It is an object of the present invention to provide a puncture needle connector with improved safety that makes it possible to easily confirm a connected state of the puncture needle container and a puncture needle and that prevents the connected state from being unintentionally cancelled. Moreover, it is another object of the present invention to provide a connecting tube equipped with this puncture needle connector.

Means for Solving Problem

A puncture needle connector of the present invention can be connected to a puncture needle having a sharp tip. The connector includes an outer cylinder, an inner cavity formed within the outer cylinder, an arm provided at the outer cylinder, the arm being elastically deformable by bending, and a claw provided on the arm. The inner cavity is in communication with an outside via a first opening and a second opening. The connector is configured such that, when the puncture needle is inserted into the inner cavity via the first opening, the claw engages with an engagement structure provided integrally with the puncture needle, a liquid-tight seal is formed between an outer circumferential surface of the puncture needle and an inner circumferential surface of the inner cavity, and the puncture needle and the second opening are in communication with each other.

The connecting tube of the present invention includes the above-described puncture needle connector of the present invention and a male connector. The male connector is in communication with the inner cavity via the second opening.

Effects of the Invention

According to the present invention, when the puncture needle is inserted into the inner cavity via the first opening, the claw engages with the engagement structure provided integrally with the puncture needle, and the liquid-tight seal is formed between the outer circumferential surface of the puncture needle and the inner circumferential surface of the inner cavity. The first opening is blocked, and thus, an infusion in the inner cavity is prevented from leaking to the outside through the first opening. It is possible to easily confirm that the liquid-tight seal is formed, by observing visually that the claw is engaged with the engagement structure. Thus, the connected state of the connector and the puncture needle can be easily confirmed. In a state in which the claw is engaged with the engagement structure, the connector and the puncture needle are prevented from being separated from each other by merely being pulled. Accordingly, the occurrence of a situation in which the connector and the puncture needle are unintentionally separated from each other, resulting in leakage of the infusion to the outside can be prevented. Thus, the connector and the connecting tube of the present invention offer improved safety.

DESCRIPTION OF THE INVENTION

Figure 1:
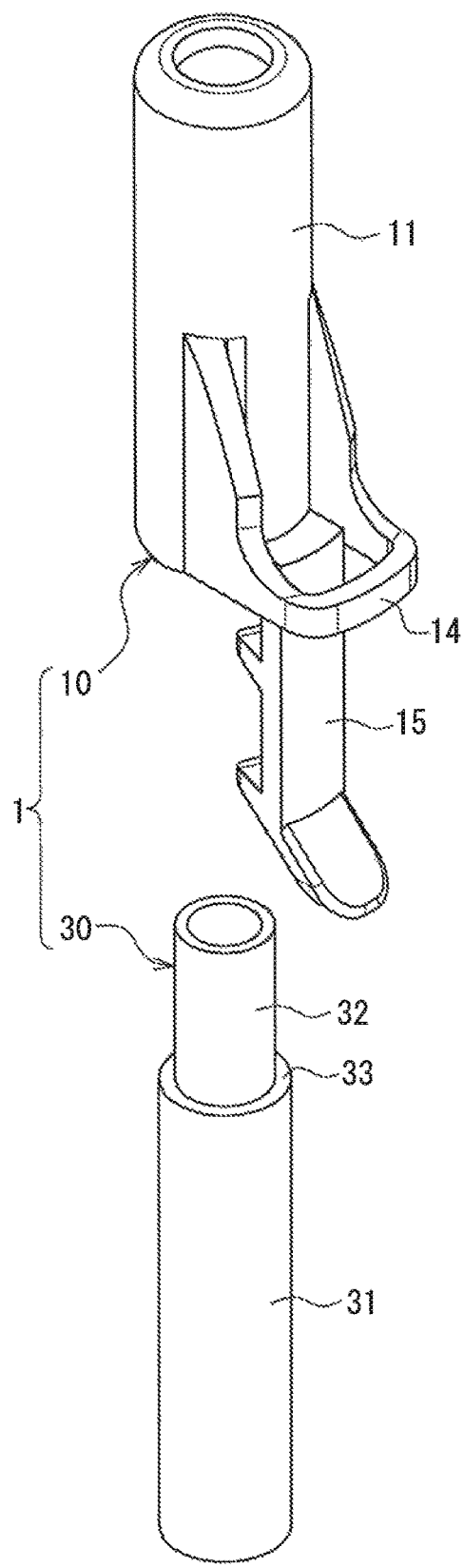
FIG. 1 is an exploded perspective view of a puncture needle connector according to an embodiment of the present invention.

In the above-described puncture needle connector of the present invention, a flexible tubular member may be provided within the outer cylinder. In this case, an inner wall of the inner cavity may be constituted by the tubular member. It is preferable that, when the puncture needle is inserted into the inner cavity via the first opening, the liquid-tight seal is formed between the puncture needle and the tubular member. Thus, a liquid-tight seal can be formed using a simple configuration. Since the tubular member constituting the inner wall of the inner cavity is disposed within the outer cylinder, an arm that is elastically deformable by bending can be formed by forming slits in the outer cylinder. In this case, the infusion in the inner cavity is prevented from leaking to the outside via the slits.

With respect to the above-described configuration, the connector of the present invention may further include a movement preventing means that prevents the tubular member from moving relative to the outer cylinder in a direction in which the puncture needle is inserted into the inner cavity via the first opening. With this configuration, during insertion of the puncture needle into the inner cavity, the tubular member is prevented from moving relative to the outer cylinder (and furthermore, also relative to the arm and the claw). Therefore, when the claw engages with the engagement structure provided integrally with the puncture needle, the liquid-tight seal can be reliably formed between the base portion of the puncture needle and the tubular member.

The claw may have an inclined surface. In this case, it is preferable that the inclined surface is inclined such that the distance from the inclined surface to the central axis of the puncture needle connector decreases in a direction in which the puncture needle is inserted into the inner cavity via the first opening. With this configuration, by simply inserting the puncture needle into the inner cavity, it is possible to engage the claw with the engagement structure, which is provided integrally with the puncture needle, without touching the claw and the arm. Therefore, the operation for connecting the connector and the puncture needle to each other can be simplified.

A plurality of the claws may be provided on the arm spaced apart from one another along a longitudinal direction (i.e., the direction in which the puncture needle is inserted into the inner cavity) of the arm. With this configuration, even with respect to a puncture needle having an engagement structure at a different position, any one of the plurality of claws can be engaged with that engagement structure. Accordingly, the number of types of puncture needles to which the connector can be connected increases.

The connector of the present invention may further include a stopper that limits the amount of bending deformation of the arm. With this configuration, plastic deformation or breakage of the arm due to excessive deformation of the arm can be prevented.

It is preferable that the inner cavity is in communication with the outside only via the first opening and the second opening. With this configuration, the infusion in the inner cavity can be reliably prevented from leaking to the outside.

In the above-described connecting tube of the present invention, the male connector may include a male member to be inserted into a coinfusion port and a lock claw that is engageable with the coinfusion port. With this configuration, in a state in which the male member is in communication with the coinfusion port, the lock claw can be engaged with the coinfusion port. Therefore, the possibility that the male connector and the coinfusion port will be unintentionally separated from each other can be reduced.

Hereinafter, the present invention will be described in detail while showing preferred embodiments thereof. However, it goes without saying that the present invention is not limited to the embodiments below. In the drawings that will be referred to in the following description, only the main members of constituent members of the embodiments of the present invention are shown in a simplified manner for the sake of convenience of description. Accordingly, the present invention may include optional members that are not shown in the drawings below. Moreover, it should be understood that the members shown in the drawings below may be modified or omitted within the scope of the present invention.

Configuration of Puncture Needle Connector

FIG. 1 is an exploded perspective view of a puncture needle connector 1 (hereinafter referred to simply as "connector 1") according to an embodiment of the present invention. The connector 1 is formed of a connector main body 10 and a tubular member 30.

Figure 2A:
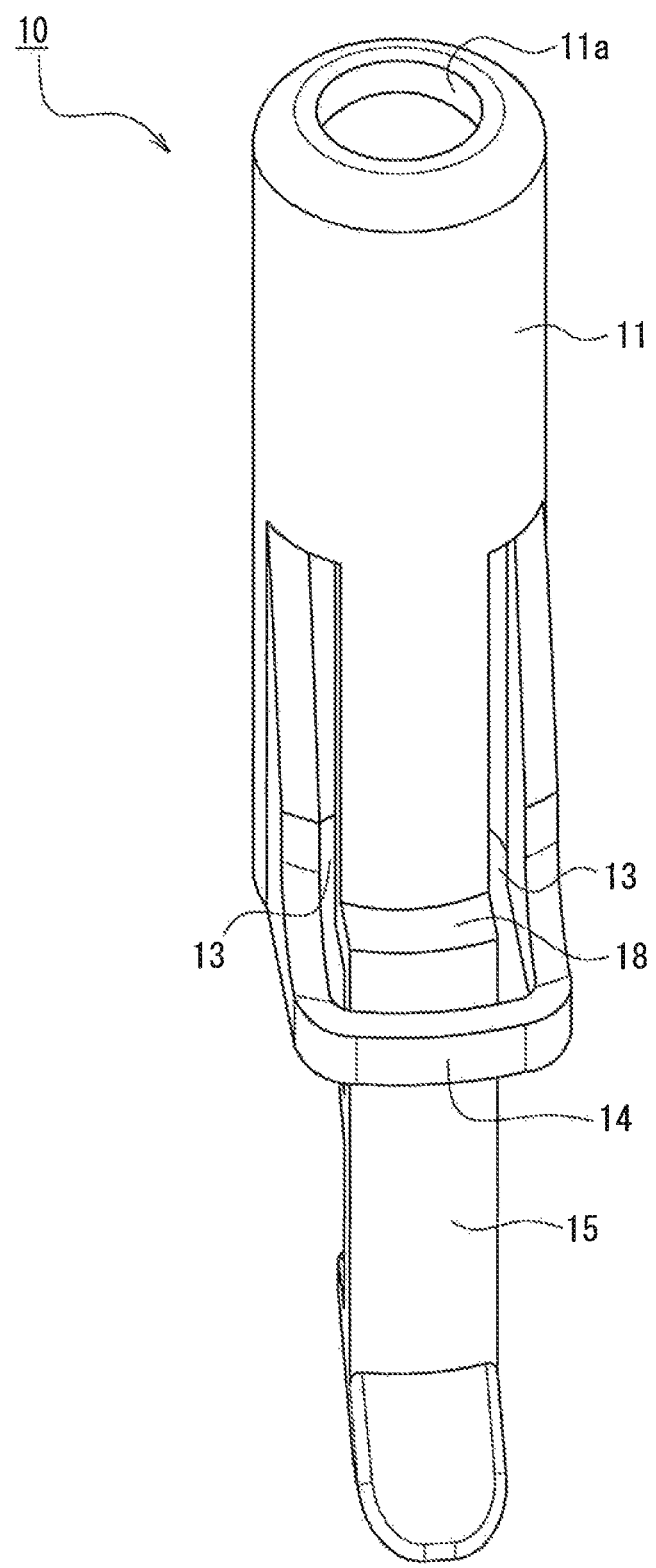
FIG. 2A is a perspective view of a connector main body constituting the puncture needle connector according to the embodiment of the present invention.
Figure 2B:
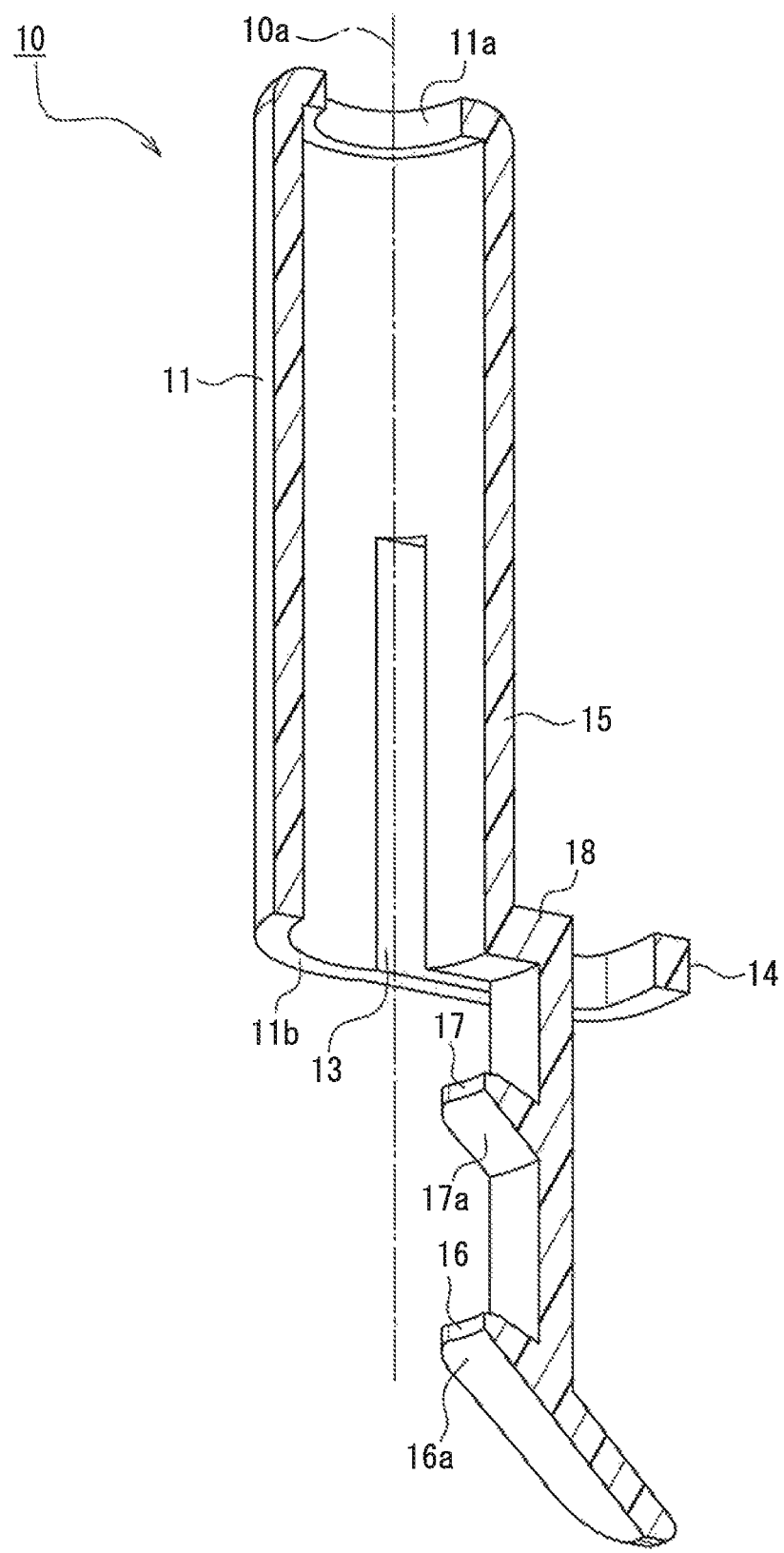
FIG. 2B is a cross-sectional perspective view of the connector main body.

FIG. 2A is a perspective view of the connector main body 10, and FIG. 2B is a cross-sectional perspective view of the connector main body 10. In FIG. 2B, a dash-and-dot line 10a represents the central axis of the connector main body 10. The central line 10a doubles as the central line of the connector 1. For the sake of convenience of the following description, a direction that is orthogonal to the central axis 10a is referred to as "radial direction", and the direction of rotation about the central axis 10a is referred to as "circumferential direction". With respect to the radial direction, the side nearer to the central axis 10a is referred to as "inner side", and the side farther from the central axis 10a is referred to as "outer side". Furthermore, the direction in which the central axis 10a extends is referred to as "vertical direction", and "up" and "down" are defined based on the direction shown in FIG. 2B. These definitions are applied not only to the connector main body 10, but also to the connector 1 including the connector main body 10 and to a connecting tube 2 (see FIG. 7, which will be described later). However, "up" and "down" do not mean the actual state in which the connector 1 or the connecting tube 2 is used.

The connector main body 10 includes an outer cylinder 11 having a cylindrical shape that opens upward and downward. In the present embodiment, an outer circumferential surface and an inner circumferential surface of the outer cylinder 11 are circular cylindrical surfaces that are coaxial with the central axis 10a. However, the present invention is not limited to this, and the outer circumferential surface and the inner circumferential surface of the outer cylinder 11 may have any shape (e.g., regular polygonal prism-shaped surfaces) other than a circular cylindrical shape. A pair of straight line-shaped slits 13 extend upward from a lower end lib of the outer cylinder 11. The pair of slits 13 are spaced apart from each other in the circumferential direction and arranged parallel to each other. The slits 13 are cut-outs penetrating the outer cylinder 11 in the radial direction. An arm 15 is sandwiched between the pair of slits 13 in the circumferential direction. The longitudinal direction of the arm 15 is parallel to the central axis 10a. The arm 15 extends further downward past the lower end lib of the outer cylinder 11.

As shown in FIG. 2B, the arm 15 has a deformed portion 18 located at substantially the same height as the lower end 11b of the outer cylinder 11. The deformed portion 18 includes two bent portions formed by bending the arm 15 at substantially right angles in opposite directions in a plane containing the central axis 10a. A portion of the arm 15 that is located below the deformed portion 18 is spaced farther apart from the central axis 10a in the radial direction than a portion of the arm 15 that is located above the deformed portion 18.

A first claw 16 and a second claw 17 protrude from the arm 15 toward the central axis 10a. The first claw 16 is provided at a lower end (leading end) of the arm 15. The second claw 17 is provided at a position between the first claw 16 and the lower end 11b of the outer cylinder 11. Downward-facing surfaces (lower surfaces) 16a and 17a of the first claw 16 and the second claw 17 are inclined surfaces that are inclined so as to slope upward toward the central axis 10a. The lower surface 16a of the first claw 16 extends outward past the arm 15.

The arm 15 has a cantilevered structure in which a portion thereof that is located at the same height as the upper end of the slit 13 serves as a fixed end, and the lower end (leading end) serves as a free end. The arm 15 is elastically deformable by bending such that the lower end thereof moves outward in the radial direction. When the arm 15 is deformed by bending in this manner, the claws 16 and 17 are displaced away from the central axis 10a.

The outer cylinder 11 is provided with a stopper 14. The stopper 14 has a substantially U-shape connecting the positions at which the pair of slits 13 of the outer cylinder 11 are respectively formed. The stopper 14 opposes an outer surface (surface on a side opposite to the central axis 10a) of the arm 15 and protrudes farther outward in the radial direction than the arm 15. In an initial state in which the arm 15 is not elastically deformed, the stopper 14 is spaced apart from the arm 15 in both the radial direction and the circumferential direction. When the arm 15 is deformed by bending such that its lower end is more largely spaced apart from the central axis 10a, the outer surface of the arm 15 collides against the stopper 14. Thus, the stopper 14 prevents the arm 15 from being excessively deformed by bending.

A small diameter portion 11a is provided at the upper end of the outer cylinder 11. The internal diameter of the small diameter portion 11a is smaller than the internal diameter of the outer cylinder 11 below the small diameter portion 11a.

The connector main body 10 is preferably made of a hard material. Although there is no limitation on the hard material, a resin material such as polycarbonate, polypropylene, polyacetal, polyamide, hard polyvinyl chloride, polyethylene, styrene-ethylene, polyethylene terephthalate, polybutylene terephthalate, or a butylene-styrene block copolymer, for example, can be used. When consideration is given to the fact that the connector main body 10 is used for medical purposes, and the arm 15 is to be elastically deformed by bending, a polyolefin resin such as polyethylene or polypropylene is preferable. Preferably, the connector main body 10 is integrally formed as a one-piece component through injection molding using the above-described resin material.

The shape of the connector main body 10 is not limited to that of the present embodiment, and can be changed as appropriate.

In the present embodiment, the arm 15 is bent into a step-like shape in the deformed portion 18. However, the shape of the arm 15 is not limited to this. For example, the arm 15 may also be curved in such a manner as to form a gently curved surface between the fixed end (upper end) and the free end (lower end) of the arm 15.

The arm 15 is formed by forming the pair of slits 13 in the outer cylinder 11. However, the arm 15 with a cantilevered structure can be formed using a configuration other than this configuration. For example, the fixed end of the arm 15 may be mounted on an outer circumferential surface of an outer cylinder 11 having a cylindrical shape in which no slits 13 are formed. In this case, the arm 15 extends downward while protruding outward in the radial direction from the outer circumferential surface of the outer cylinder 11.

In the present embodiment, the arm 15 is provided with the two claws 16 and 17. However, the number of claws may be one or three or more. Preferably, the claw that is located at the lowest position is provided at the leading end (lower end) of the arm 15. In the case where a plurality of claws are provided, the plurality of claws may be arranged spaced apart from one another in the vertical direction within a region between the leading end (lower end) of the arm 15 and the lower end 11b of the outer cylinder 11.

In the present embodiment, the stopper 14 is provided at the same height as the lower end 11b of the outer cylinder 11. However, the position of the stopper 14 in the vertical direction is not limited to this position. As long as the arm 15 can be restricted from being excessively deformed by bending, the stopper 14 may be provided at a higher position than the lower end 11b, or may be provided at a lower position than the lower end 11b. The shape of the stopper 14 when viewed along the central axis 10a needs not be a substantially U-shape that is fixed to the outer cylinder 11 at both ends thereof. For example, a configuration may also be adopted in which the stopper 14 has a substantially L-shape or a substantially J-shape and is fixed to the outer cylinder 11 at only one end thereof. In the present invention, the stopper 14 may be omitted.

Figure 3:
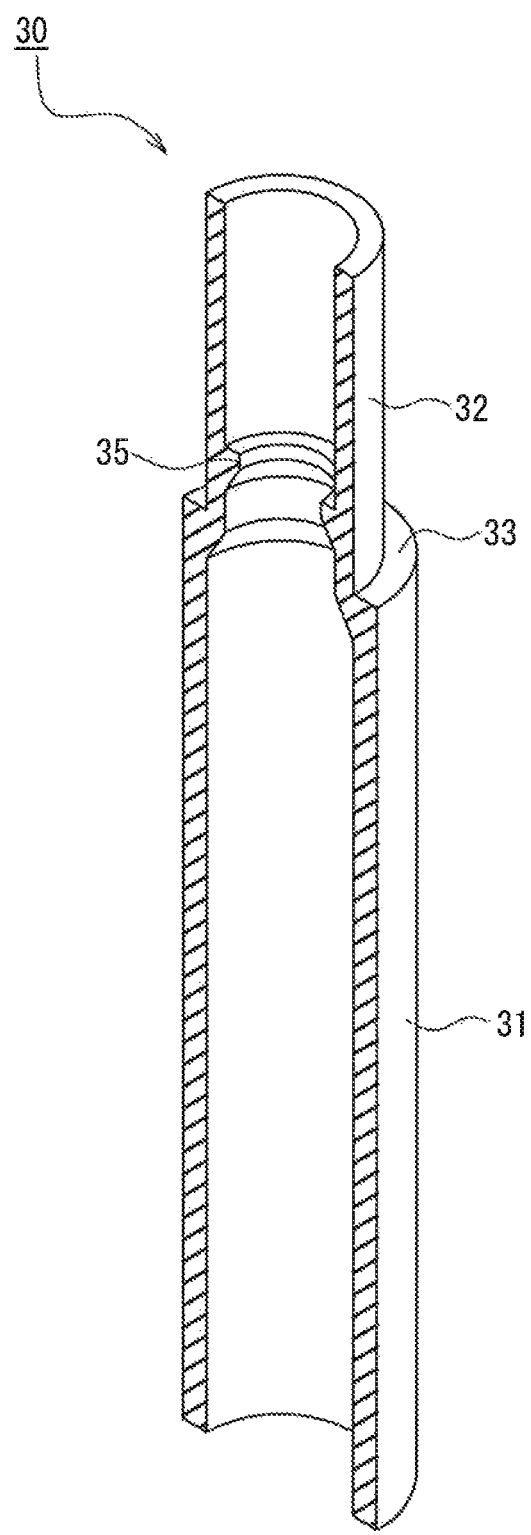
FIG. 3 is a cross-sectional perspective view of a tubular member constituting the puncture needle connector according to the embodiment of the present invention.

FIG. 3 is a cross-sectional perspective view of the tubular member 30. The tubular member 30 has a cylindrical shape whose upper and lower ends are open. The tubular member 30 includes a large tube portion 31 on the lower side and a small tube portion 32 on the upper side. The large tube portion 31 and the small tube portion 32 both have a circular cylindrical shape, and are coaxially connected together in a liquid-tight manner. The large tube portion 31 has a larger internal diameter and a larger external diameter than the small tube portion 32. The external diameter of the large tube portion 31 is preferably equal to or smaller than the internal diameter of the outer cylinder 11 of the connector main body 10 and also is preferably larger than the internal diameter of the small diameter portion 11a of the connector main body 10. The external diameter of the small tube portion 32 is preferably equal to or smaller than the internal diameter of the small diameter portion 11a of the connector main body 10.

A step 33 is formed at the boundary between the large tube portion 31 and the small tube portion 32 due to the difference between the external diameters of the large tube portion 31 and the small tube portion 32. A projection 35 is provided on the inner circumferential surface of the small tube portion 32 at a position near the large diameter portion 31. In the present embodiment, the projection 35 is an annular projection that is continuous in the circumferential direction. However, the projection 35 needs not be continuous in the circumferential direction and may also be divided at one or a plurality of positions in the circumferential direction.

The tubular member 30 (at least the large tube portion 31) is made of a flexible material that has pliability. For example, a soft material such as vinyl chloride, a rubber material, such as isoprene rubber, silicone rubber, or butyl rubber, or a thermoplastic elastomer, such as a styrene elastomer, an olefin elastomer, or a polyurethane elastomer, may be used. The method for producing the tubular member 30 is not limited. For example, a method (integral molding method) in which the entire tubular member 30 is integrally molded at one time as a one-piece component, a method (coinjection molding method) in which the large tube portion 31 and the small tube portion 32 are integrated through coinjection molding, a method (connecting method) in which the large tube portion 31 and the small tube portion 32 are separately formed and then connected together in a liquid-tight manner, and the like may be used. In the coinjection molding method and the connecting method, the large tube portion 31 and the small tube portion 32 may be formed using the same material or may be formed using different materials. For example, it is possible to form the large diameter portion 31 using the above-described flexible material and form the small tube portion 32 using a relatively hard material (e.g., the same material as the material of the above-described connector main body 10). In the connecting method, in order to connect the large tube portion 31 and the small tube portion 32 that have been separately formed, any method such as a method that uses an adhesive or a method in which the two portions are fusion-bonded to each other may be used, for example.

As shown in FIG. 1, the tubular member 30 is inserted, with the small tube portion 32 pointing upward, into the outer cylinder 11 of the connector main body 10 from the lower opening of the outer cylinder 11.

Figure 4A:
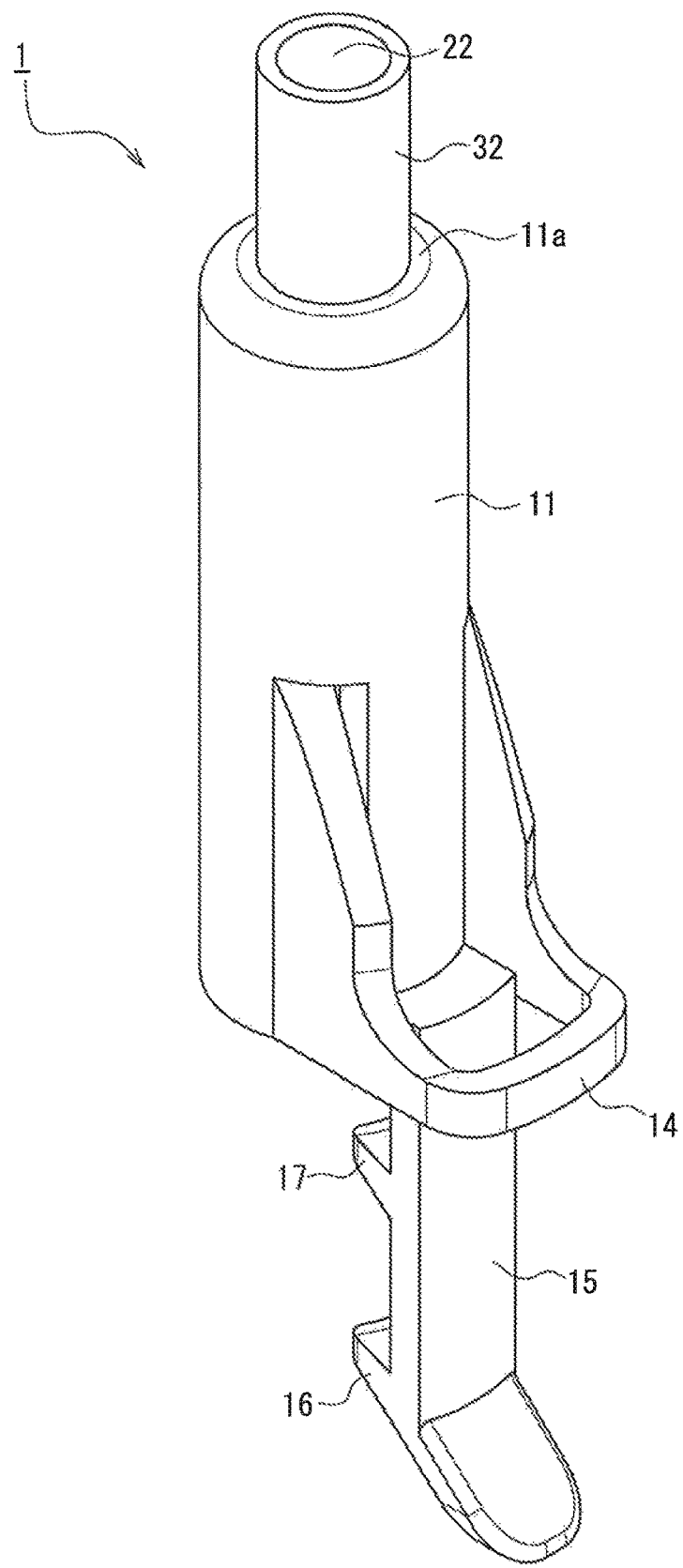
FIG. 4A is a perspective view of the puncture needle connector according to the embodiment of the present invention when viewed from above.
Figure 4B:
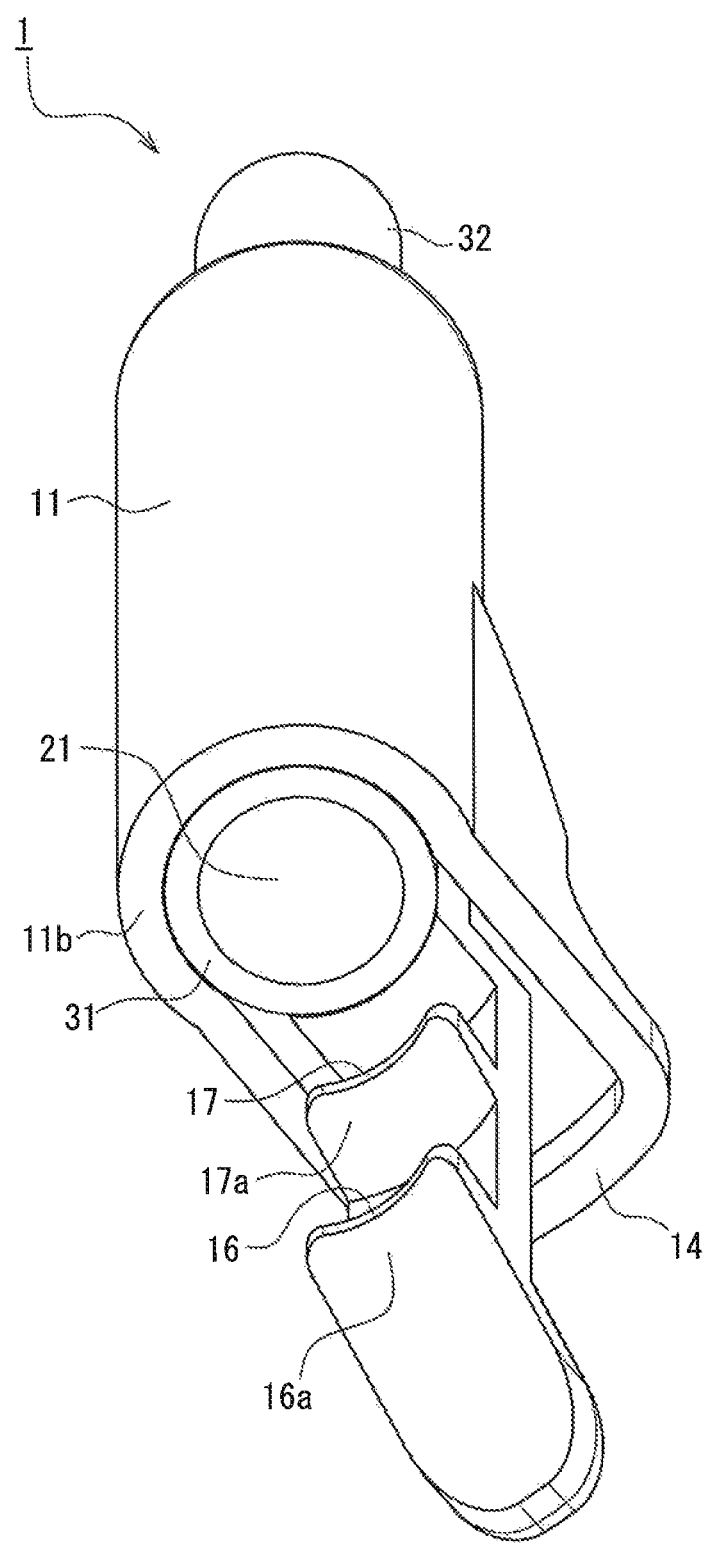
FIG. 4B is a perspective view of the puncture needle connector connector when viewed from below.
Figure 4C:
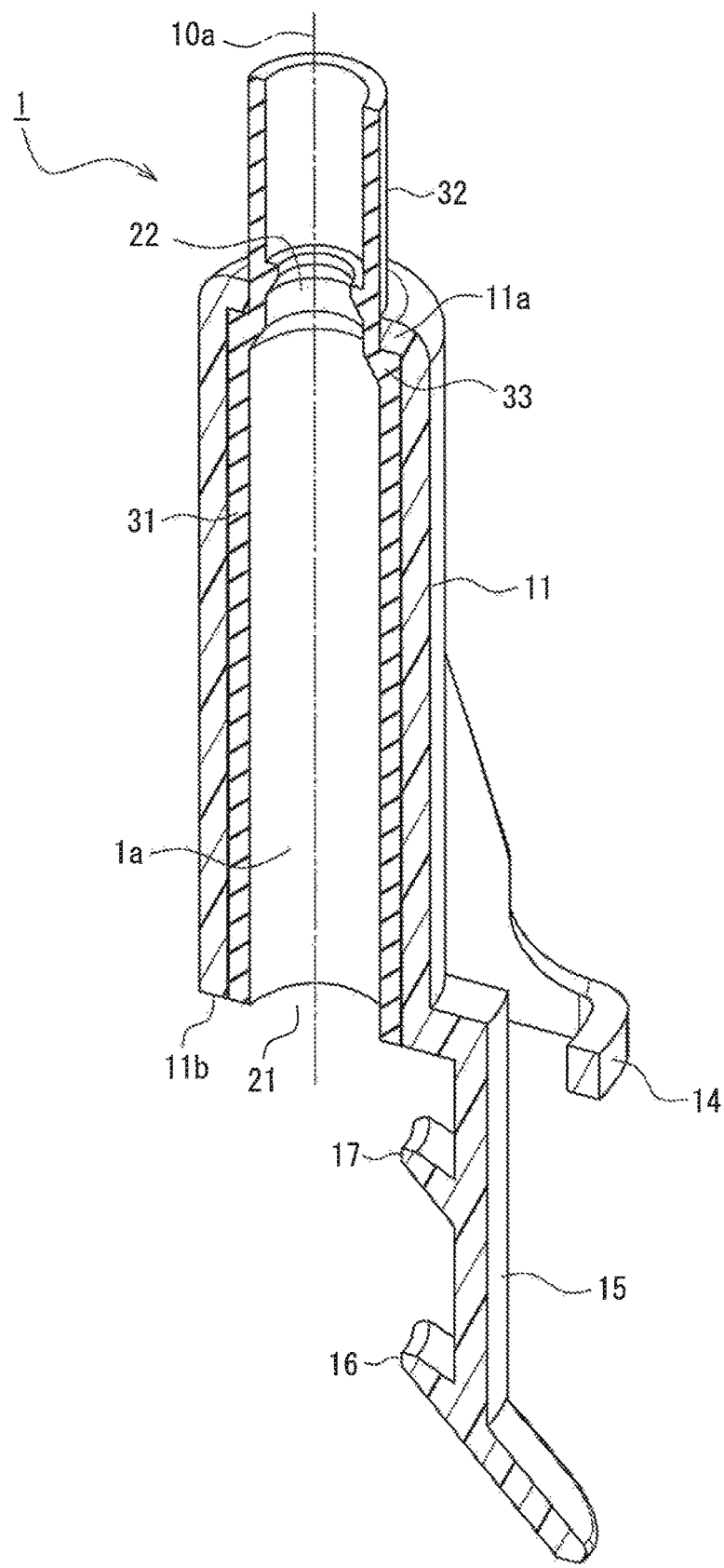
FIG. 4C is a cross-sectional perspective view of the puncture needle connector connector.

FIG. 4A is a perspective view of the connector 1 when viewed from above, FIG. 4B is a perspective view of the connector 1 when viewed from below, and FIG. 4C is a cross-sectional perspective view of the connector 1. As is best shown in FIG. 4C, the large tube portion 31 of the tubular member 30 is housed within the outer cylinder 11. The small tube portion 32 of the tubular member 30 passes through the small diameter portion 11a of the outer cylinder 11 and protrudes farther upward than the connector main body 10. The step 33 of the tubular member 30 is engaged with the small diameter portion 11a. Thus, the large tube portion 31 is prevented from moving out upward through the small diameter portion 11a. In a state in which the step 33 abuts against the small diameter portion 11a in the vertical direction, the lower end of the tubular member 30 (i.e., the large tube portion 31) is located at substantially the same position in the vertical direction as the lower end 11b of the outer cylinder 11.

In the present embodiment, an inner cavity 1a of the connector 1 is defined by the tubular member 30 (in particular, the large tube portion 31 of the tubular member 30). An inner wall of the inner cavity 1a is constituted by the inner circumferential surface, which has a circular cylindrical shape, of the large tube portion 31. The slits 13 formed in the outer cylinder 11 are blocked by the tubular member 30. The inner cavity 1a is in communication with the outside only via a first opening (lower opening of the large tube portion 31) 21 through which the puncture needle 210 (see FIG. 7, which will be described later) of an infusion set 200 is to be inserted and a second opening (i.e., upper opening (on the small tube portion 32 side) of the large diameter portion 31) 22 to which a tube 9 (see FIGS. 5A and 5B, which will be described later) is to be connected.

Configuration of Connecting Tube

Figure 5A:
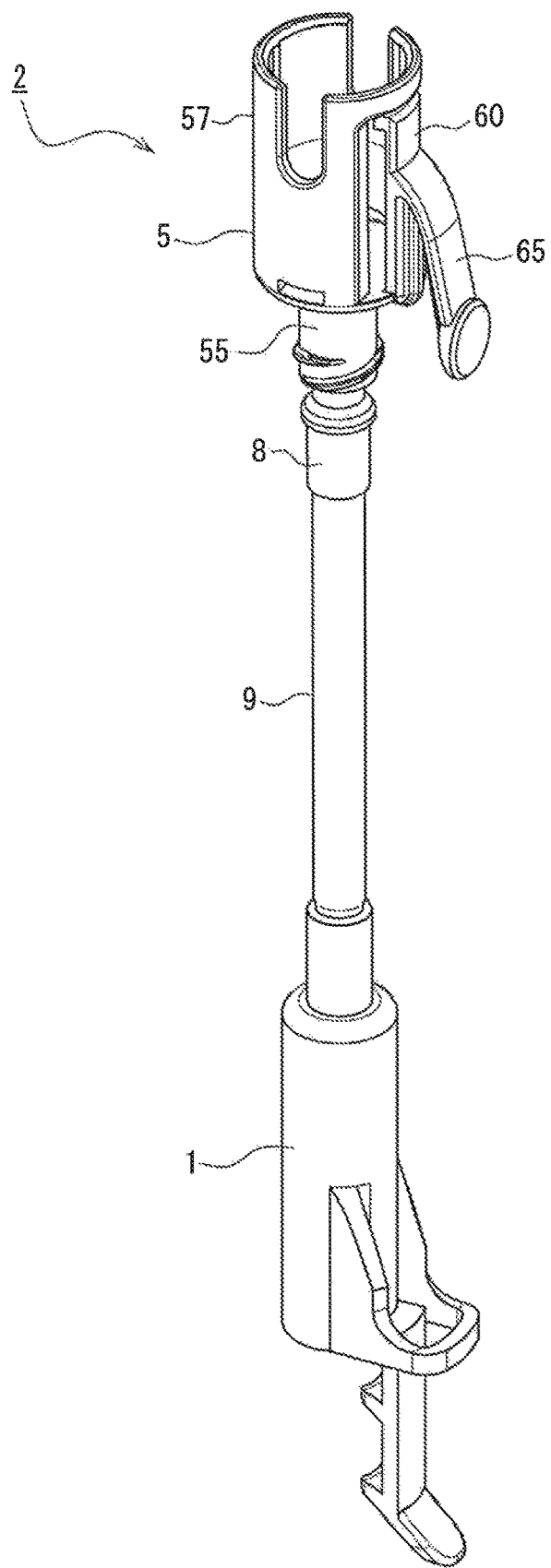
FIG. 5A is a perspective view of a connecting tube according to an embodiment of the present invention.
Figure 5B:
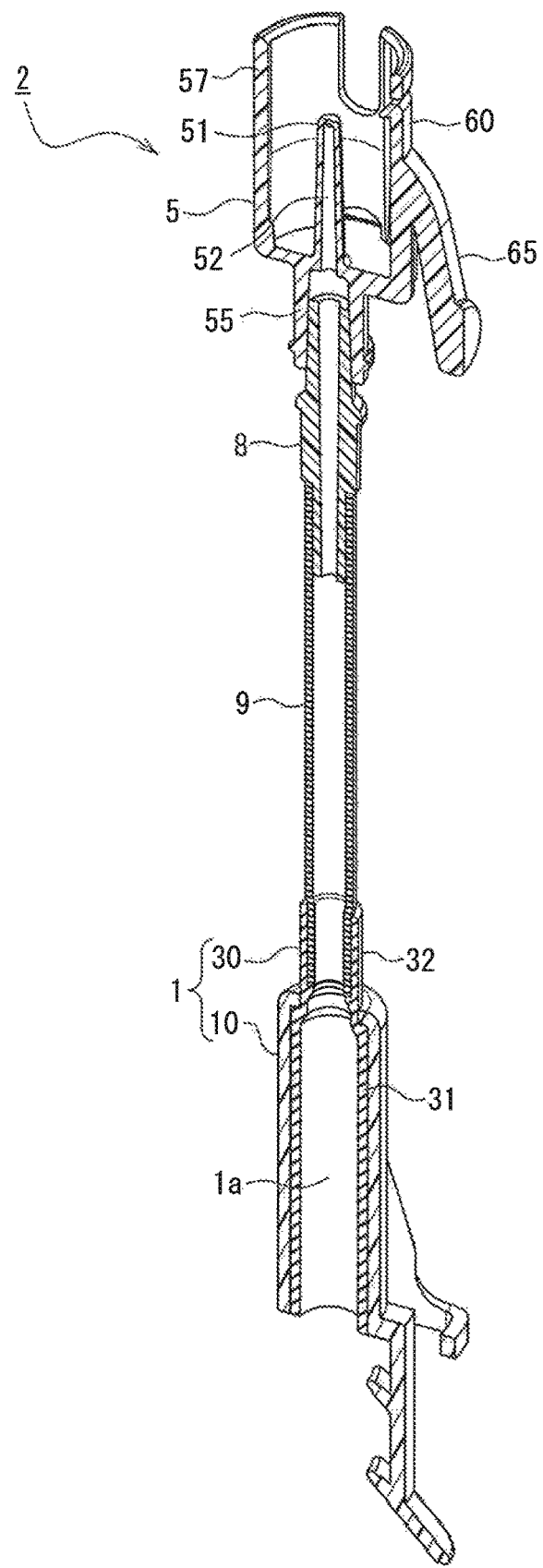
FIG. 5B is a cross-sectional perspective view of the connecting tube.

FIG. 5A is a perspective view of the connecting tube 2 according to an embodiment of the present invention, and FIG. 5B is a cross-sectional perspective view of the connecting tube 2. The connecting tube 2 includes the above-described connector 1, a male connector 5, and the tube 9 that connects the connector 1 and the male connector 5 to each other.

As is the case with a tube constituting an infusion set, the tube 9 is a hollow cylindrical object that is flexible (or pliable) to such an extent that it can be easily deformed. There is no limitation on the material of the tube 9. In general, a rubber-like elastic soft material (so-called elastomer) can be used, and, for example, rubber, such as natural rubber, isoprene rubber, or silicone rubber, a thermoplastic elastomer, such as a styrene elastomer, an olefin elastomer, or a polyurethane elastomer, soft polyvinyl chloride, or the like can be used.

A lower end of the tube 9 is connected to the tubular member 30 of the connector 1. More specifically, as shown in FIG. 5B, the lower end of the tube 9 is inserted into the small tube portion 32 of the tubular member 30. The tube 9 is inserted into the small tube portion 32 until the lower end of the tube 9 collides against the projection 35 (see FIG. 3) protruding from the inner circumferential surface of the small tube portion 32. Thus, the insertion depth of the tube 9 into the small tube portion 32 can be set to be constant. The tube 9 and the small tube portion 32 are fixed to each other using any method such as application of an adhesive or fusion bonding. Thus, the inner cavity 1a (see FIG. 4C) of the male connector 1 and the tube 9 are connected to each other in a liquid-tight manner.

Figure 6A:
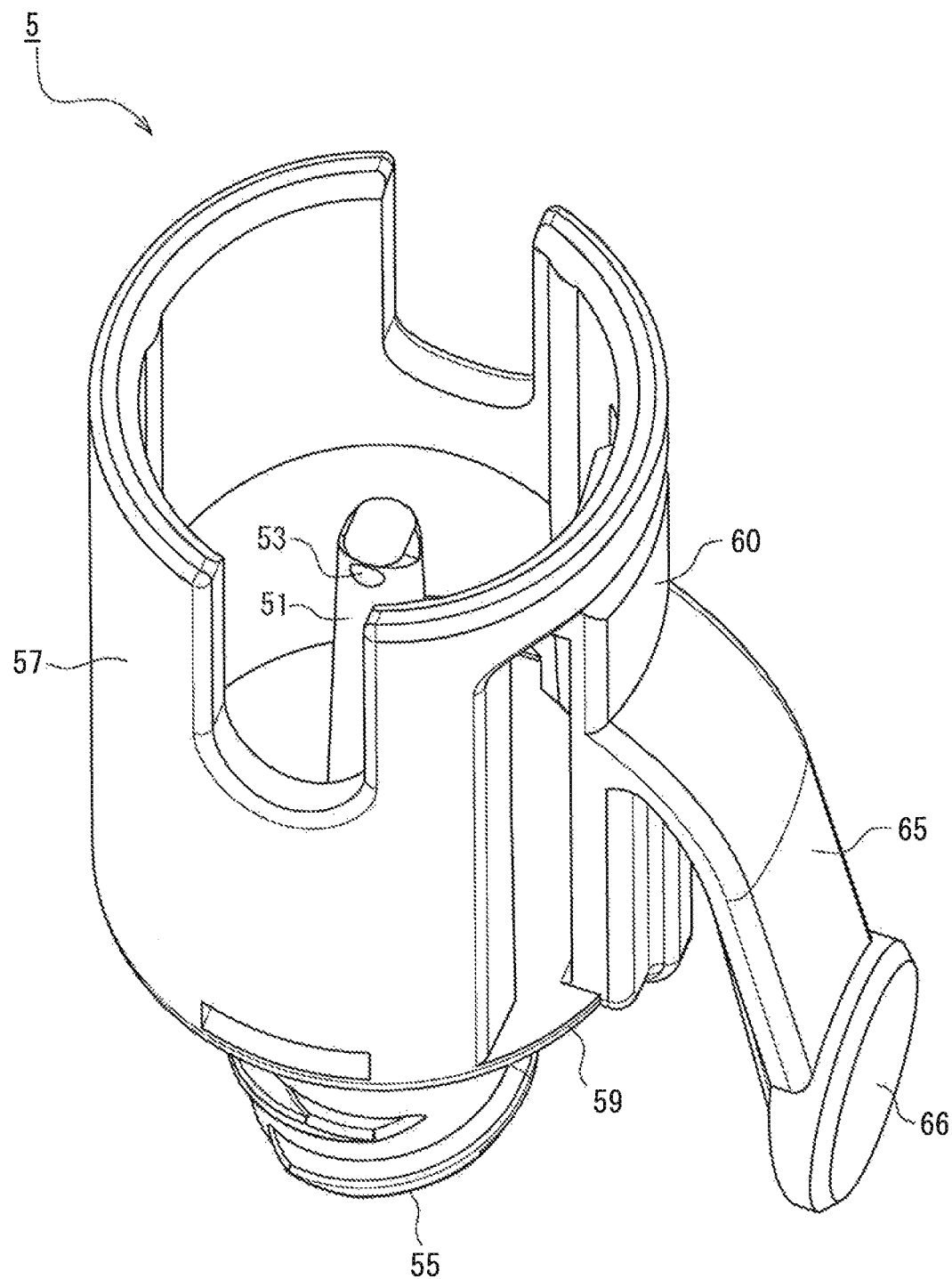
FIG. 6A is a perspective view of a male connector constituting the connecting tube according to the embodiment of the present invention.
Figure 6B:
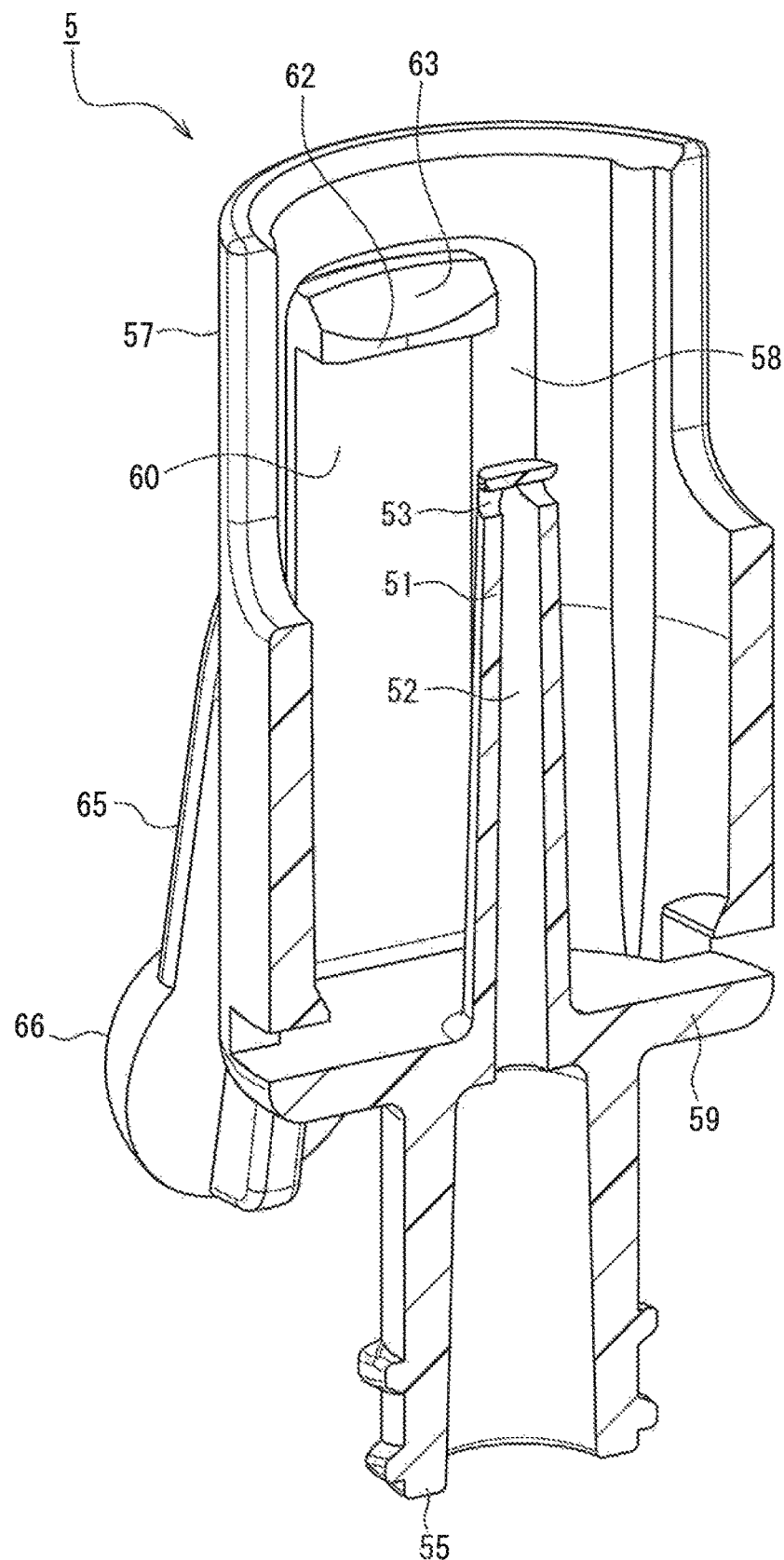
FIG. 6B is a cross-sectional perspective view of the male connector.
Figure 6C:
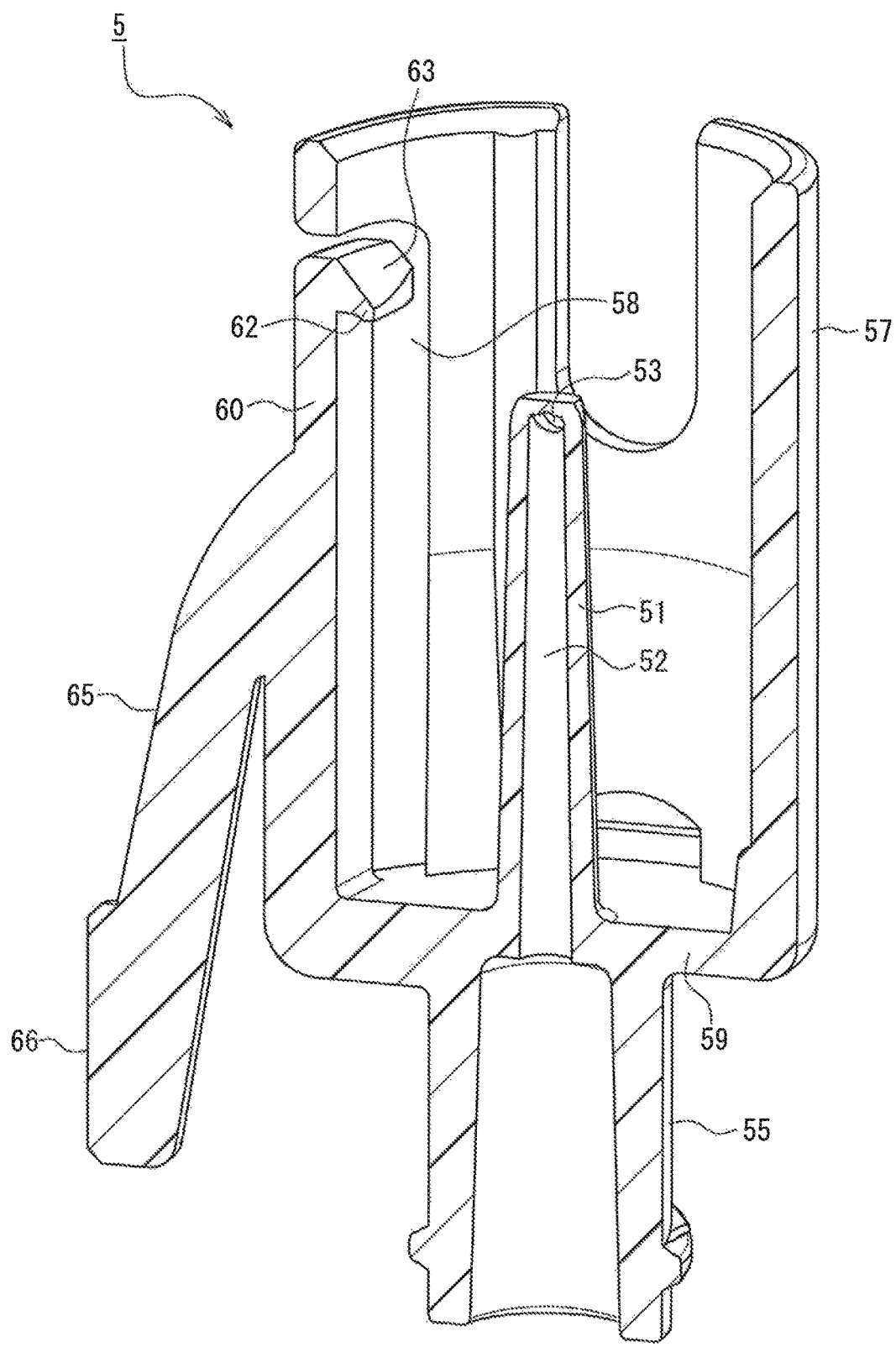
FIG. 6C is a cross-sectional perspective view of the male connector when viewed from a different direction.

Now, the male connector 5 will be described. FIG. 6A is a perspective view of the male connector 5, and FIGS. 6B and 6C are cross-sectional perspective views of the male connector 5.

A male luer (male member) 51 and a hood 57 are provided on a base plate 59 that has a substantially circular shape. The male luer 51 is a rod-shaped member. A flow channel 52 is formed within the male luer 51 along the longitudinal direction thereof. A lateral hole 53 is formed near a leading end of the male luer 51 and penetrates the male luer 51 in the radial direction. The lateral hole 53 is in communication with the flow channel 52.

A cylindrical portion 55 is provided on a side of the base plate 59 that is opposite to the male luer 51. The cylindrical portion 55 has a hollow circular cylindrical shape that is coaxial with the male luer 51, and is in communication with the flow channel 52 of the male luer 51. An inner circumferential surface of the cylindrical portion 55 constitutes a tapered surface (so-called female tapered surface) whose internal diameter increases as the distance from the base plate 59 increases.

The hood 57 has a hollow circular cylindrical shape that is coaxial with the male luer 51, and surrounds the male luer 51. An inner circumferential surface (surface opposing the male luer 51) of the hood 57 has an internal diameter substantially equal to or slightly larger than the external diameters of a cap 170 and an annular projection 153 of a coinfusion port 150 of an adapter 100, which will be described later.

A substantially U-shaped slit 58 is formed in the hood 57. The slit 58 is a hole penetrating the hood 57 in the radial direction. Thus, a lock lever 60 surrounded by the slit 58 is formed. The lock lever 60 opposes the male luer 51 and extends substantially parallel to the male luer 51. The lock lever 60 has a cantilevered structure in which its end on the base plate 59 side serves as a fixed end, and an end opposite to the fixed end serves as a free end. A lock claw 62 protrudes from the leading end (free end) of the lock lever 60 toward the male luer 51. The lock claw 62 has an inclined surface 63 at an edge on a side opposite to the base plate 59, the inclined surface 62 being inclined such that the distance from the male luer 51 increases as the distance from the base plate 59 increases. An operating arm 65 is provided on a surface of the lock lever 60 that is opposite to the male luer 51. The operating arm 65 extends downward past the base plate 59 so as to oppose the cylindrical portion 55. An operating portion 66 is provided at a leading end of the operating arm 65. When the operating portion 66 is pressed toward the cylindrical portion 55, the lock lever 60 elastically bends and deforms, and the lock claw 62 is displaced away from the male luer 51.

As shown in FIGS. 5A and 5B, the upper end of the tube 9 is connected to the cylindrical portion 55 of the male connector 5. In the present embodiment, the cylindrical portion 55 and the tube 9 are connected to each other via a hard connecting cylinder 8. The connecting cylinder 8 is a cylindrical member in which a through hole (flow channel) is formed along the longitudinal direction. At an outer circumferential surface of one end (upper end) of the connecting cylinder 8, a tapered surface (so-called male tapered surface) whose external diameter decreases as the distance to the leading end decreases is formed, while at an outer circumferential surface of the other end (lower end) of the connecting cylinder 8, a circular cylindrical surface is formed. The male tapered surface is inserted into the cylindrical portion 55, and the circular cylindrical surface is inserted into the tube 9. Thus, the male luer 51, the cylindrical portion 55, the connecting cylinder 8, the tube 9, and the inner cavity 1a of the connector 1 are in communication with each other in this order.

The male connector 5 and and the connecting cylinder 8 are preferably made of a hard material. Although there is no limitation on the hard material, a resin material such as polycarbonate, polypropylene, polyacetal, polyamide, hard polyvinyl chloride, polyethylene, styrene-ethylene, polyethylene terephthalate, polybutylene terephthalate, or a butylene-styrene block copolymer can be used, for example. It is preferable that each of the male connector 5 and and the connecting cylinder 8 is integrally formed as a one-piece component through injection molding using the above-described resin material.

In the present embodiment, the cylindrical portion 55 and the tube 9 are connected to each other via the connecting cylinder 8. However, the cylindrical portion 55 and the tube 9 may be connected to each other via any desired member other than the connecting cylinder 8. Alternatively, the cylindrical portion 55 and the tube 9 may be directly connected to each other.

Method of Usage of Connecting Tube

Figure 7:
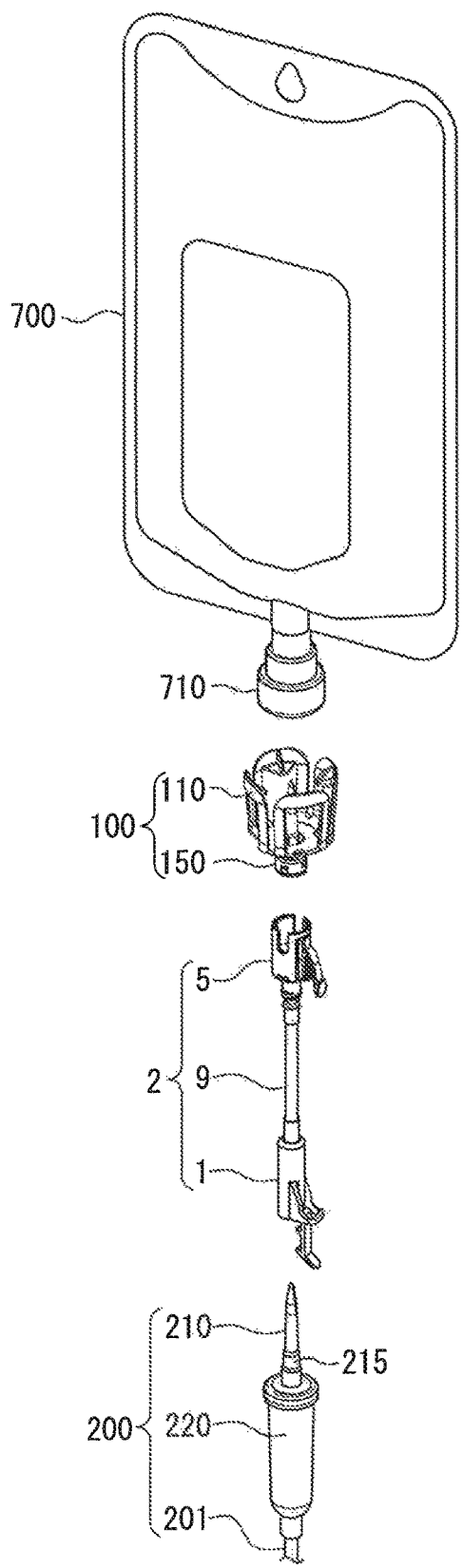
FIG. 7 is an exploded perspective view illustrating a method of usage of the connecting tube according to the embodiment of the present invention.

FIG. 7 is an exploded perspective view illustrating a method of usage of the connecting tube 2.

An infusion to be administered to a patient is reserved in an infusion container 700. A female connector 710 is provided at a lower end of the infusion container 700. An opening of the female connector 710 is sealed with a rubber stopper (not visible in FIG. 7). The adapter 100 is attached to the female connector 710.

The infusion set 200 has, at its upstream end, a puncture needle 210 having a sharp tip. A needle (not shown) to be inserted into a vein of the patient is provided at a downstream end of the infusion set 200. The puncture needle 210 and the needle at the downstream end are in communication with each other via a flexible tube 201 through which the infusion flows. In the present example, an intravenous cylinder 220 is provided integrally with the puncture needle 210. The intravenous cylinder 220 makes the flow of the infusion flowing through the infusion set 200 visible. Although not shown in the drawings, the tube 201 may also be provided with a clamp for adjusting the flow rate of the infusion flowing through the infusion set 200, a filter for filtering the infusion, and the like.

The connecting tube 2 is interposed between the adapter 100 and the infusion set 200, and is used to connect the adapter 100 and the infusion set 200 to each other.

Figure 8A:
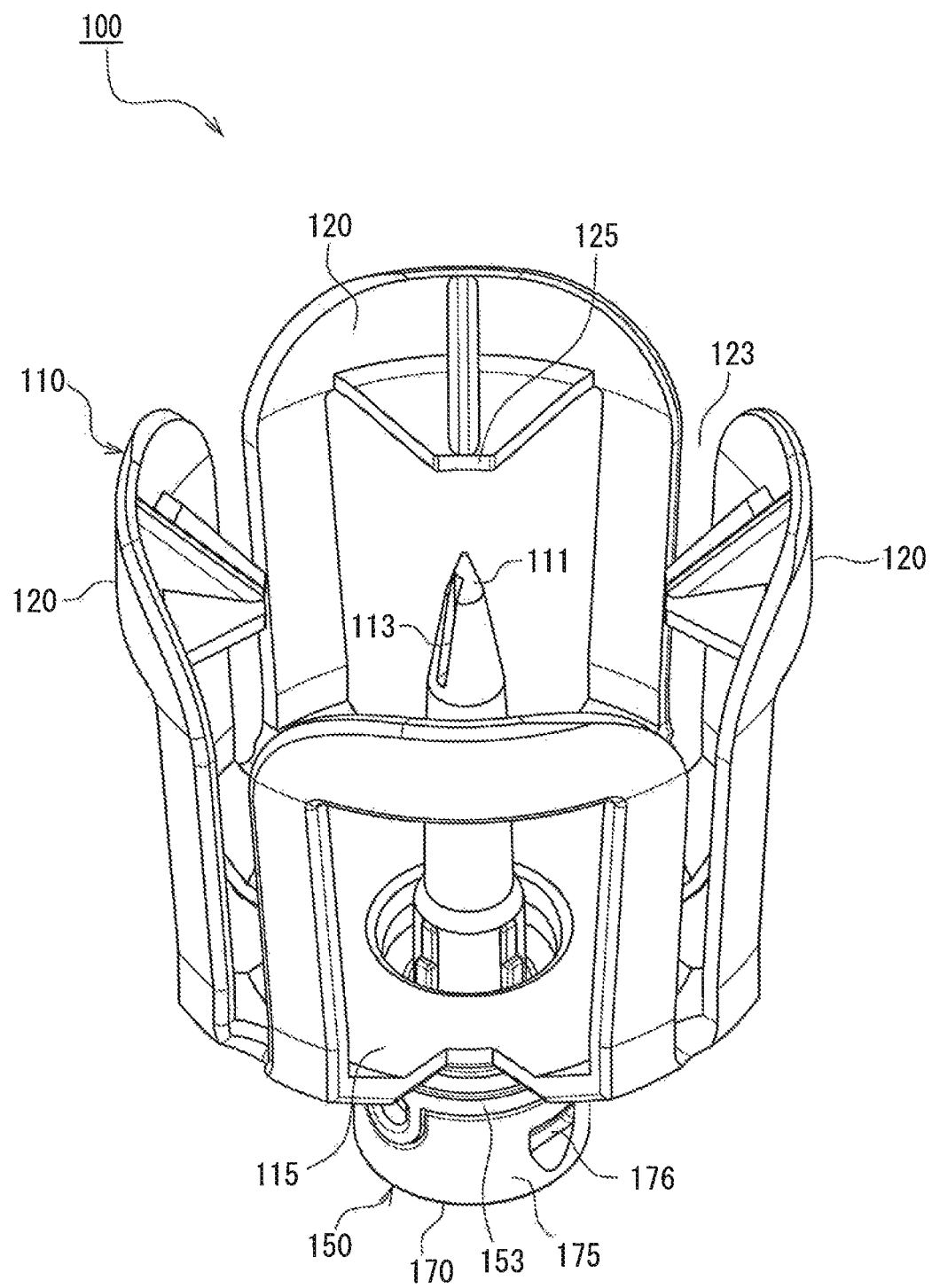
FIG. 8A is a perspective view of an adapter when viewed from a certain direction.
Figure 8B:
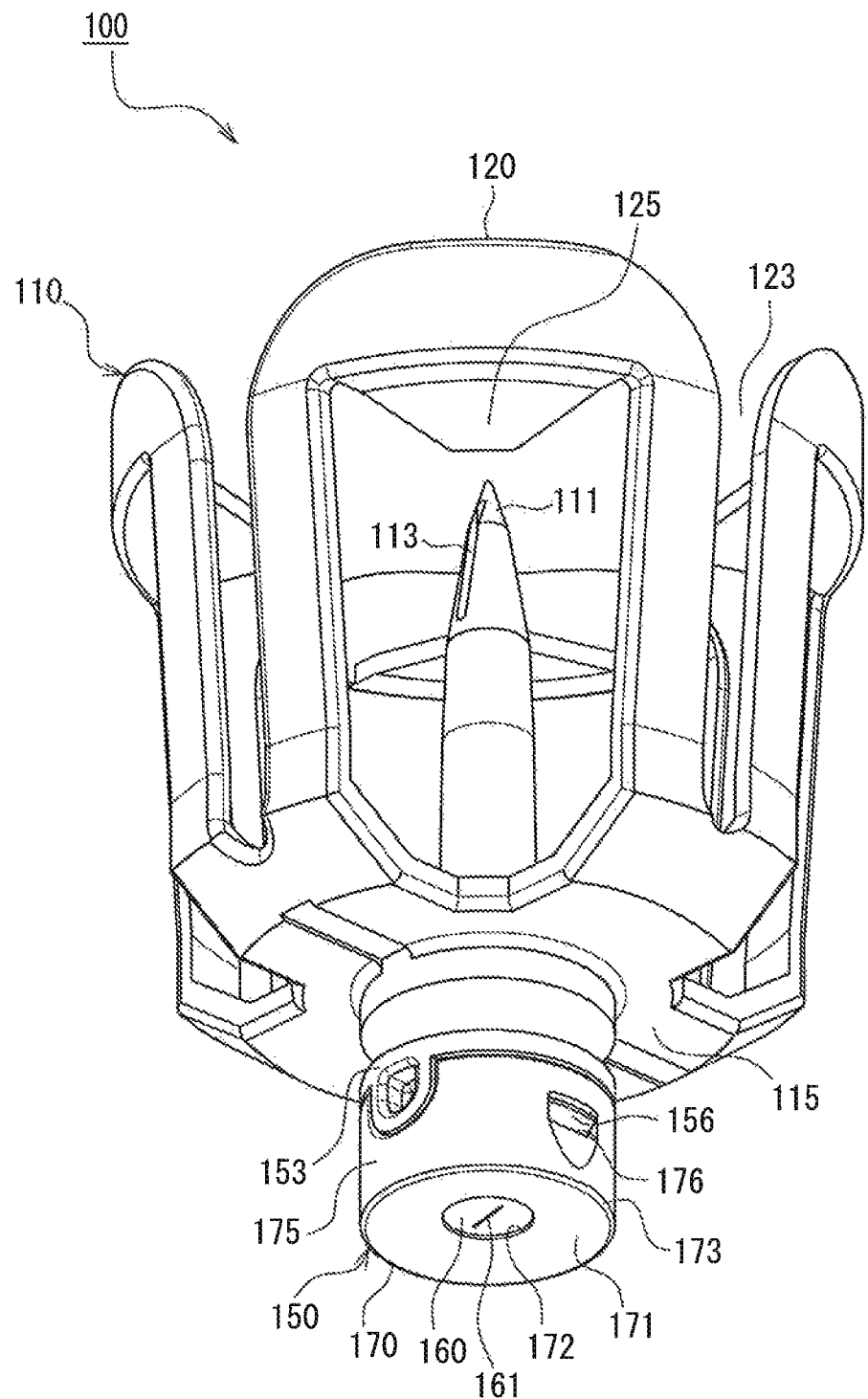
FIG. 8B is a perspective view of the adapter when viewed from a different direction.
Figure 8C:
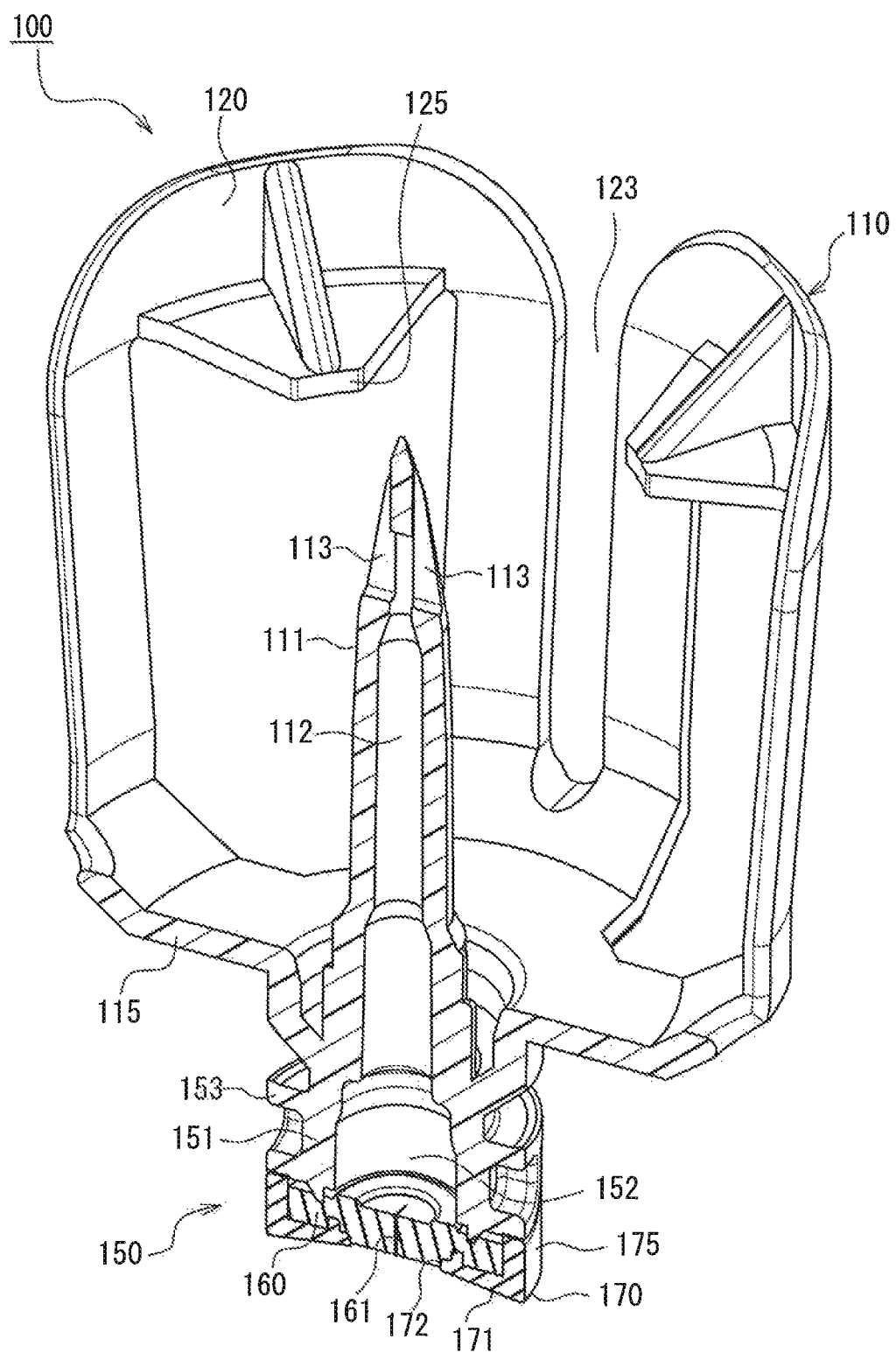
FIG. 8C is a cross-sectional perspective view of the adapter.

Now, the adapter 100 will be described. FIG. 8A is a perspective view of the adapter 100 when viewed from a certain direction, FIG. 8B is a perspective view of the adapter 100 when viewed from a different direction, and FIG. 8C is a cross-sectional perspective view of the adapter 100.

The adapter 100 includes an adapter main body 110 involved in the connection to the female connector 710 (see FIG. 7) and the coinfusion port 150 involved in the connection to the male connector 5 of the connecting tube 2.

The adapter main body 110 includes a puncture needle 111, four substantially-U-shaped arms 120 opposing the puncture needle 111, and engaging claws 125 protruding from the respective arms 120 toward the puncture needle 111.

The puncture needle 111 has a sharp tip so that a rubber stopper 715 (see FIG. 9) of the female connector 710 can be pierced therewith. A flow channel 112 through which the infusion flows is formed inside the puncture needle 111 along the longitudinal direction of the puncture needle 111. Two lateral holes 113 penetrating the puncture needle 111 in its diameter direction are formed in a tapered portion near the tip of the puncture needle 111. The lateral holes 113 are in communication with the flow channel 112.

A base plate 115 is provided at a base portion of the puncture needle 111. The base plate 115 is a thin plate extending in a direction (hereinafter referred to as "radial direction") that is orthogonal to the longitudinal direction of the puncture needle 111. The four arms 120 extend from an outer circumferential edge of the base plate 115 toward the same side as the puncture needle 111. Each arm 120 has a substantially U-shape as a whole. The arms 120 are arranged equiangularly around the puncture needle 111 so as to surround the puncture needle 111. The arms 120 adjacent to each other in the circumferential direction are spaced apart from each other via a slit 123.

The engaging claws 125 are provided in leading end portions (portions that are the farthest away from the base plate 115) of the respective arms 120. The engaging claws 125 protrude from surfaces opposing the puncture needle 111 of the respective arms 120 toward the puncture needle 111.

Each arm 120 has a cantilevered structure in which its connection portion connected to the base plate 115 serves as a fixed end. Each arm 120 can be elastically deformed in a direction in which its claw 125 moves away from the puncture needle 111. Since the slits 123 are provided between adjacent arms 120, the arms 120 can be deformed independently of one another.

The number of arms 120 needs not be four, and may be more than four or less than four. The shape of each arm 120 needs not be a substantially U-shape, and may also be, for example, a narrow plate-like shape (rectangular strip-like shape) with a cantilevered structure.

As is best shown in FIG. 8C, the coinfusion port 150 includes a cylindrical portion 151 having a substantially circular cylindrical shape, a septum (partition wall member) 160 provided at a leading end of the cylindrical portion 151, and the cap 170 with which the septum 160 is covered.

An annular projection 153 and a pair of projections 156 (see FIG. 8B) protrude outward from an outer circumferential surface of the cylindrical portion 151. The annular projection 153 is slightly spaced apart from the projections 156 toward the base end (toward the puncture needle 111). The annular projection 153 is a projection that is continuous in the circumferential direction.

The septum 160 is a thin plate made of an elastic material such as rubber and having a circular shape in plan view. A straight-line shaped slit (cut) 161 penetrating the septum 160 in its thickness direction is formed at the center of the septum 160.

As shown in FIG. 8B, the cap 170 has a top plate 171 having a circular plate-like shape, and a peripheral wall 175 extending from an outer circumferential edge 173 of the top plate 171 and having a circular cylindrical shape. A circular opening (through hole) 172 is formed at the center of the top plate 171. A pair of holes 176 are formed in the peripheral wall 175. The holes 176 are through holes that penetrate the peripheral wall 175 in the radial direction.

As can be understood from FIG. 8C, the septum 160 is attached to the leading end of the cylindrical portion 151, and the cap 170 is attached to the cylindrical portion 151 so as to cover the septum 160. The projections 156 of the cylindrical portion 151 are fitted into the respective holes 176 provided in the peripheral wall 175 of the cap 170, and the projections 156 are engaged with edges of the respective holes 176 (see FIG. 8B). The septum 160 is sandwiched between the leading end of the cylindrical portion 151 and the top plate 171 of the cap 170 in the thickness direction. The slit 161 of the septum 160 is exposed in the opening 172 of the cap 170 (see FIG. 8B). The annular projection 153 formed on the cylindrical portion 151 is adjacent to the peripheral wall 175 of the cap 170. A top surface of the annular projection 153 constitutes a circular cylindrical surface that is substantially flush with the outer circumferential surface of the peripheral wall 175.

The male connector 5 (see FIGS. 6A to 6C) can be connected to the coinfusion port 150 (see FIG. 11, which will be described later). The male luer 51 of the male connector 5 is inserted into the slit 161 of the septum 160. The annular projection 153 functions as an engagement structure with which the lock claw 62 of the male connector 5 is engaged. When the lock claw 62 is disengaged from the annular projection 153 by operating the operating arm 65 of the male connector 5, the male connector 5 can be separated from the coinfusion port 150. When the male luer 51 is withdrawn from the septum 160, the septum 160 immediately returns to its initial state, and the slit 161 is closed in a liquid-tight manner. In this manner, the septum 160 functions as a self-closing valve. The self-closing coinfusion port 150 equipped with this septum 160 is also called a "needleless port".

The adapter 100 may also be the same as the known adapter disclosed in Patent Document 1.

Figure 9:
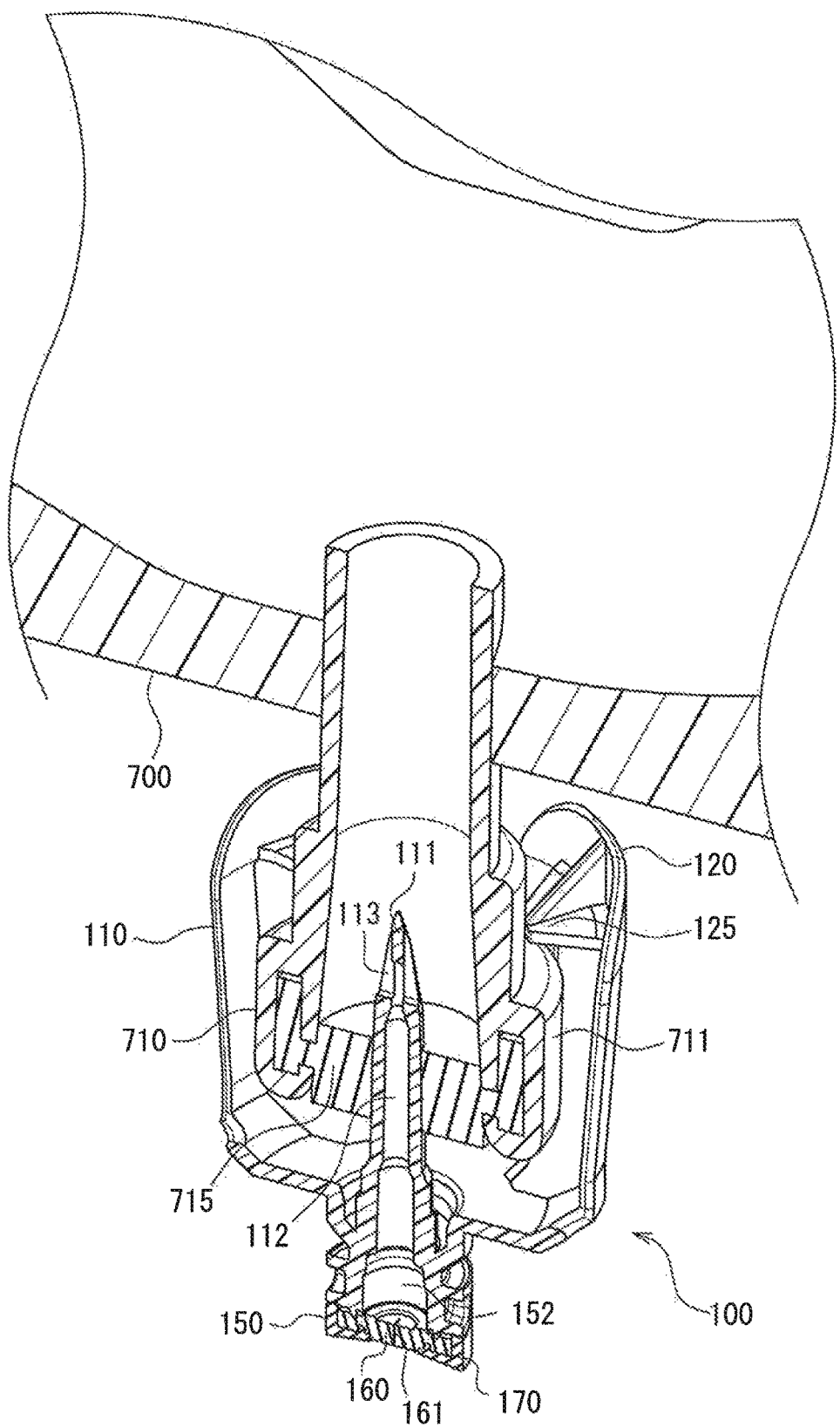
FIG. 9 is a cross-sectional perspective view showing a state in which the adapter is attached to a female connector of an infusion container.

In FIG. 7, the adapter 100 is attached to the female connector 710 first. FIG. 9 is a cross-sectional perspective view showing a state in which the adapter 100 is attached to the female connector 710. The puncture needle 111 penetrates the rubber stopper 715 that seals the opening of the female connector 710. The lateral holes 113 provided near the tip of the puncture needle 111 have passed through the rubber stopper 715 and are exposed on the infusion container 700 side. Therefore, the infusion container 700 and the inner cavity 152 of the coinfusion port 150 are in communication with each other via the flow channel 112 of the puncture needle 111. Since the slit 161 of the septum 160 is closed, the infusion in the infusion container 700 is prevented from leaking to the outside through the slit 161.

The engaging claws 125 provided on the arms 120 are engaged with a circular cylindrical, large diameter portion 711 where the diameter of the female connector 710 is increased. Accordingly, even if an external force (e.g., pulling force acting in a direction in which the female connector 710 and the adapter 100 are separated from each other), vibration, or the like is applied to the female connector 710 and the adapter 100, the puncture needle 111 is prevented from unintentionally coming off the rubber stopper 715. The arms 120 elastically bend and deform as appropriate in accordance with the external diameter of the female connector 710.

Next, in FIG. 7, the puncture needle 210 of the infusion set 200 is connected to the connector 1 of the connecting tube 2. Specifically, the puncture needle 210 is inserted into the inner cavity 1a (i.e., the large tube portion 31, see FIG. 4C) of the connector 1.

Figure 10A:
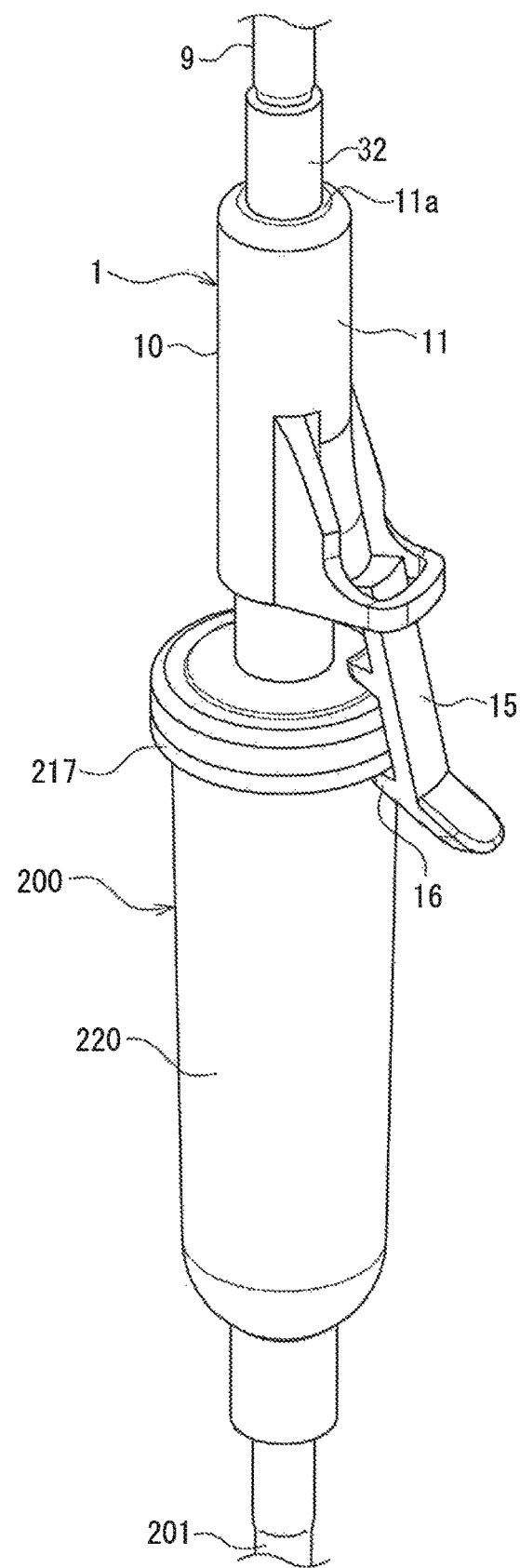
FIG. 10A is a perspective view showing a state in which the puncture needle connector according to the embodiment of the present invention is connected to a puncture needle of an infusion set.
Figure 10B:
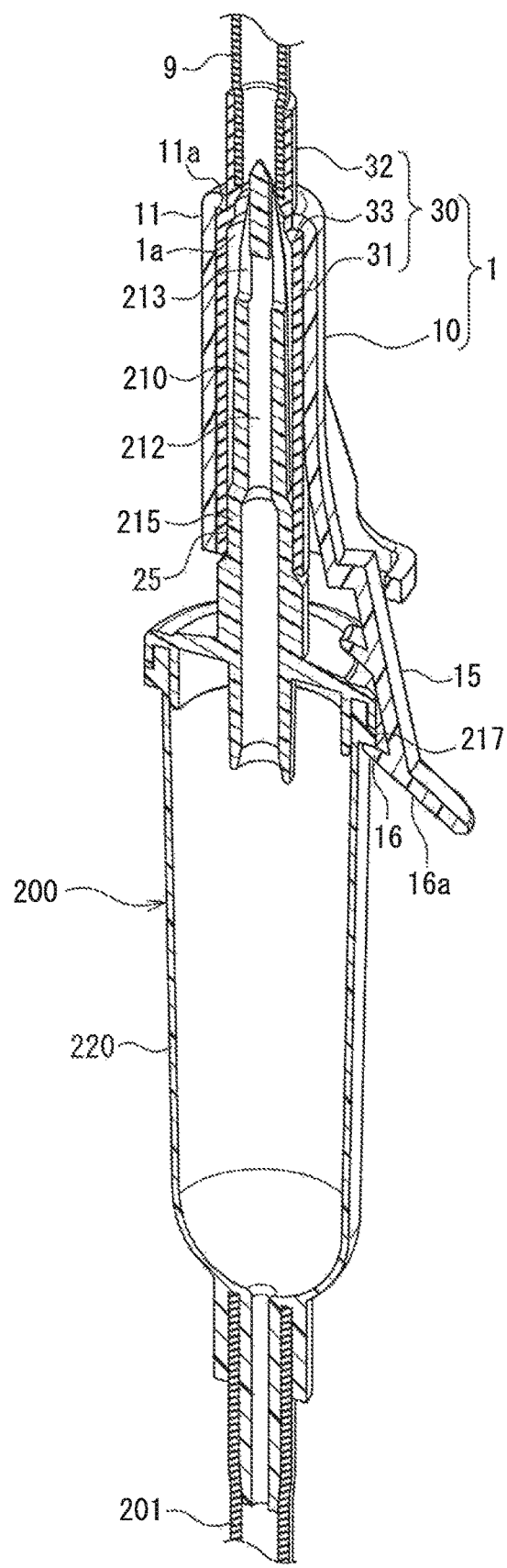
FIG. 10B is a cross-sectional perspective view showing the state in FIG. 10A.

FIG. 10A is a perspective view showing a state in which the connector 1 and the puncture needle 210 are connected to each other, and FIG. 10B is a cross-sectional perspective view showing this state.

As shown in FIG. 10B, the puncture needle 210 has substantially the same configuration as the puncture needle 111 of the adapter 100. That is to say, the puncture needle 210 has a sharp tip so that it is also possible to directly pierce the rubber stopper 715 of the female connector 710 therewith. A flow channel 212 through which the infusion flows is formed inside the puncture needle 210 along the longitudinal direction of the puncture needle 210. Two lateral holes 213 penetrating the puncture needle 210 in its diameter direction are formed in a tapered portion near the tip of the puncture needle 210. The lateral holes 213 are in communication with the flow channel 212.

The puncture needle 210 has a base portion 215 near its base end (end that is opposite to the tip of the puncture needle 210). An outer circumferential surface of the base portion 215 constitutes a circular cylindrical surface whose diameter is slightly larger than that of a portion nearer to the tip than the base portion 215. The base portion 215 is inserted into the large tube portion 31 of the tubular member 30 of the connector 1. Preferably, the internal diameter of the large tube portion 31 is slightly smaller than the external diameter of the base portion 215. Thus, as a result of the base portion 215 being inserted into the large tube portion 31, the large tube portion 31 is stretched in the circumferential direction so that its diameter is increased. Therefore, a liquid-tight seal 25 is formed between the inner circumferential surface of the tubular member 30 (in particular, the large tube portion 31) and the outer circumferential surface of the base portion 215. The lower, first opening 21 (see FIG. 4C) of the inner cavity 1a of the connector 1 is sealed with the base portion 215 in a liquid-tight manner.

The external diameter of the portion of the puncture needle 210 in which the lateral holes 213 are formed is smaller than the internal diameter of the tubular member 30. For this reason, the flow channel 212 of the puncture needle 210 is in communication with the inner cavity 1a of the connector 1 via the lateral holes 213.

The first claw 16 provided on the arm 15 of the connector 1 is engaged with an increased-diameter portion 217. Thus, even if tension is applied between the connecting tube 2 and the infusion set 200, the connector 1 and the puncture needle 210 are prevented from separating from each other. In the present embodiment, the increased-diameter portion 217 is provided on the intravenous cylinder 220. The puncture needle 210 is integrated with the intravenous cylinder 220. As a result, the increased-diameter portion 217 is provided substantially integrally with the puncture needle 210.

As can be easily understood from FIG. 10B, when insertion of the puncture needle 210 into the inner cavity 1a of the connector 1 is started, the inclined surface 16a of the first claw 16 collides against the increased-diameter portion 217. As the puncture needle 210 is further inserted, the first claw 16 is displaced outward while the inclined surface 16a slides on the increased-diameter portion 217, and the arm 15 elastically bends and deforms accordingly. Then, when the first claw 16 has moved over the increased-diameter portion 217, the elastic restoring force of the arm 15 brings the first claw 16 into engagement with the increased-diameter portion 217 as shown in FIG. 10B. In this manner, since the first claw 16 is provided with the inclined surface 16a, the first claw 16 can be automatically engaged with the increased-diameter portion 217 without touching the arm 15 and the first claw 16 with hand, by simply inserting the puncture needle 210 into the inner cavity 1a of the connector 1.

Since the step 33 formed on the outer circumferential surface of the tubular member 30 collides against the small diameter portion 11a of the outer cylinder 11, in the process of inserting the puncture needle 210 into the inner cavity 1a, the tubular member 30 is prevented from moving upward (in the direction in which the puncture needle 210 is inserted into the inner cavity 1a) relative to the outer cylinder 11 (and furthermore the connector main body 10). Therefore, when the first claw 16 is engaged with the increased-diameter portion 217, the liquid-tight seal 25 is reliably formed between the base portion 215 and the tubular member 30.

Next, in FIG. 7, the male connector 5 of the connecting tube 2 is connected to the coinfusion port 150 of the adapter 100.

Figure 11:
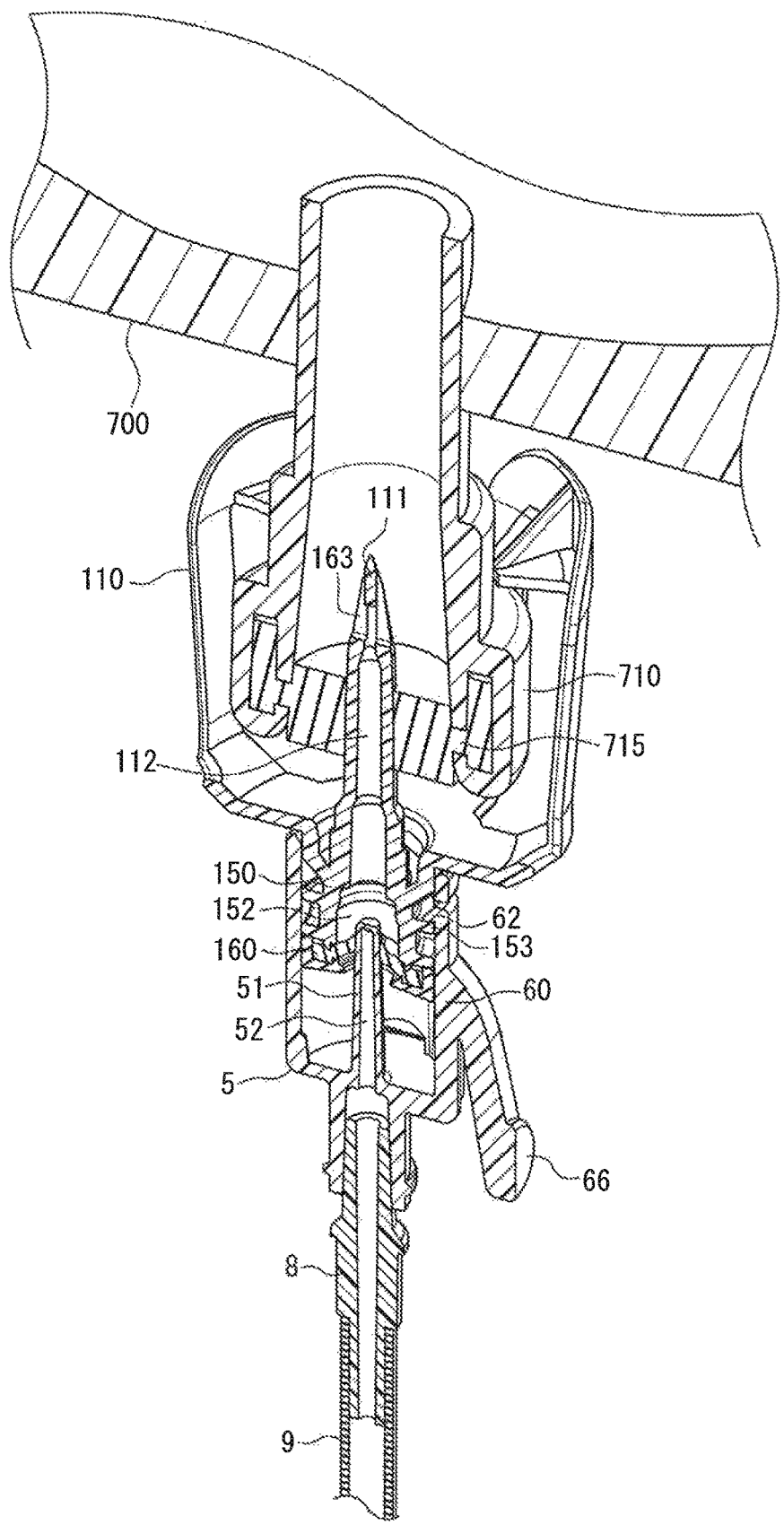
FIG. 11 is a cross-sectional perspective view showing a state in which the male connector constituting the connecting tube according to the embodiment of the present invention is connected to a coinfusion port of the adapter.

FIG. 11 is a cross-sectional perspective view showing a state in which the male connector 5 and the coinfusion port 150 are connected to each other. As can be understood from FIGS. 6B and 6C, when the coinfusion port 150 is inserted into the hood 57, the outer circumferential edge 173 (see FIG. 8B) of the top plate 171 of the cap 170 collides against the inclined surface 63 (see FIG. 6C) of the lock claw 62 protruding from the lock lever 60. While sliding on the inclined surface 63, the outer circumferential edge 173 causes the lock lever 60 to elastically bend and deform in a direction in which the lock claw 62 moves away from the male luer 51. When the lock claw 62 finished passing the annular projection 153 of the coinfusion port 150, the lock lever 60 returns to the initial shape, and the lock claw 62 engages with the annular projection 153.

The male luer 51 of the male connector 5 penetrates the slit 161 of the septum 160, and the lateral hole 53 (see FIG. 6B) of the male luer 51 is exposed in the inner cavity 152 of the coinfusion port 150. Therefore, the coinfusion port 150 and the flow channel 52 of the male luer 51 are in communication with each other. The septum 160 is elastically deformed due to the male luer 51 being inserted therein.

Figure 12:
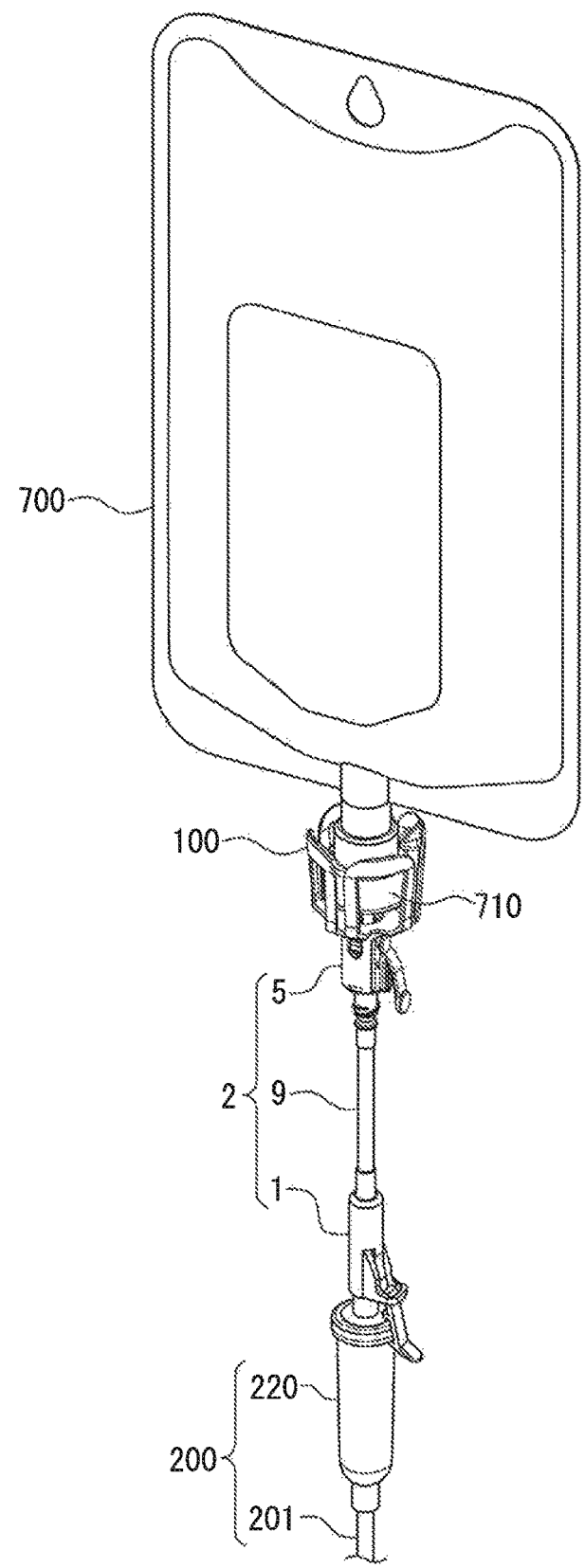
FIG. 12 is a perspective view showing a state in which the infusion container and the infusion set are connected to each other using the adapter and the connecting tube according to the embodiment of the present invention.

FIG. 12 is a perspective view showing a state in which the female connector 710 of the infusion container 700 and the infusion set 200 are connected to each other via the adapter 100 and the connecting tube 2. In this state, the needle (not shown) provided at the downstream end of the infusion set 200 is inserted into a vein of the patient. Then, the clamp (not shown) provided on the infusion set 200 is opened. The infusion in the infusion container 700 flows through the adapter 100, the connecting tube 2, and the infusion set 200 in this order and is administered to the patient.

Note that the connector 1 and the puncture needle 210 can be separated from each other by elastically bending and deforming the arm 15 so that the first claw 16 moves away from the central axis 10a and thereby disengaging the first claw 16 from the increased-diameter portion 217 (see FIGS. 10A and 10B). Moreover, the male connector 5 and the adapter 100 can be separated from each other by pressing the operating portion 66 to elastically bend and deform the lock lever 60 so that the lock claw 62 moves away from the male luer 51 and thereby disengaging the lock claw 62 from the coinfusion port 150 (see FIG. 11).

Effects

The inner cavity 1a of the connector 1 is in communication with the outside only via the first opening 21, which opens downward, and the second opening 22, which opens upward (see FIG. 4C). When the puncture needle 210 is inserted into the inner cavity 1a via the first opening 21, the liquid-tight seal 25 is formed between the outer circumferential surface of the base portion 215 of the puncture needle 210 and the inner circumferential surface of the tubular member 30, which defines the inner cavity 1a. Thus, the first opening 21 is blocked by the puncture needle 210 in a liquid-tight manner. The infusion is prevented from leaking to the outside from between the first opening 21 and the base portion 215. The flow channel 212 of the puncture needle 210 is in communication with the second opening 22 via the inner cavity 1a. Furthermore, the second opening 22 is in communication with the male connector 5 via the tube 9. Therefore, in the state shown in FIG. 12, the infusion in the infusion container 700 can be administered to the patient without leaking to the outside.

The connector 1 includes the first claw 16, which is engageable with the increased-diameter portion 217 (engagement structure) provided integrally with the puncture needle 210. At substantially the same time as the liquid-tight seal 25 is formed between the base portion 215 of the puncture needle 210 and the tubular member 30, the first claw 16 engages with the increased-diameter portion 217 (see FIG. 10B). In other words, when the puncture needle 210 is inserted into the inner cavity 1a of the connector 1 until the first claw 16 engages with the increased-diameter portion 217, the liquid-tight seal 25 is formed between the base portion 215 and the tubular member 30. Thus, the connected state of the connector 1 and the puncture needle 210 can be judged by confirming whether or not the first claw 16 is engaged with the increased-diameter portion 217. The engagement of the first claw 16 with the increased-diameter portion 217 can be confirmed visually with ease. Therefore, in the present embodiment, the connected state of the connector 1 and the puncture needle 210 can be confirmed easily.

Then, once the first claw 16 engages with the increased-diameter portion 217, the connector 1 and the puncture needle 210 are prevented from being separated from each other merely due to tension being applied between the connecting tube 2 and infusion set 200. Therefore, the occurrence of a situation in which the puncture needle 210 unintentionally comes off the connector 1, resulting in leakage of the infusion to the outside can be prevented. Thus, the safety is improved.

Furthermore, the male connector 5 includes the lock claw 62, which engages with the coinfusion port 150 when the male luer 51 is in communication with the inner cavity 152 of the coinfusion port 150. For this reason, once the lock claw 62 engages with the coinfusion port 150, the male connector 5 and the coinfusion port 150 are prevented from being separated from each other merely due to tension being applied between the connecting tube 2 and the infusion container 700. Therefore, the occurrence of a situation in which the male luer 51 unintentionally comes off the coinfusion port 150, resulting in leakage of the infusion to the outside can be prevented. In this respect as well, the safety is improved.

The intravenous cylinder 220 may also be attached to a flow rate controller. The flow rate controller measures the infusion flowing through the intravenous cylinder 220. Thus, the flow rate of the infusion flowing through the infusion set 200 can be controlled. In the present embodiment, since the connector 1 is provided with only a single arm 15, the intravenous cylinder 220 can be attached to the flow rate controller without causing the arm 15 to collide against the flow rate controller.

Figure 13:
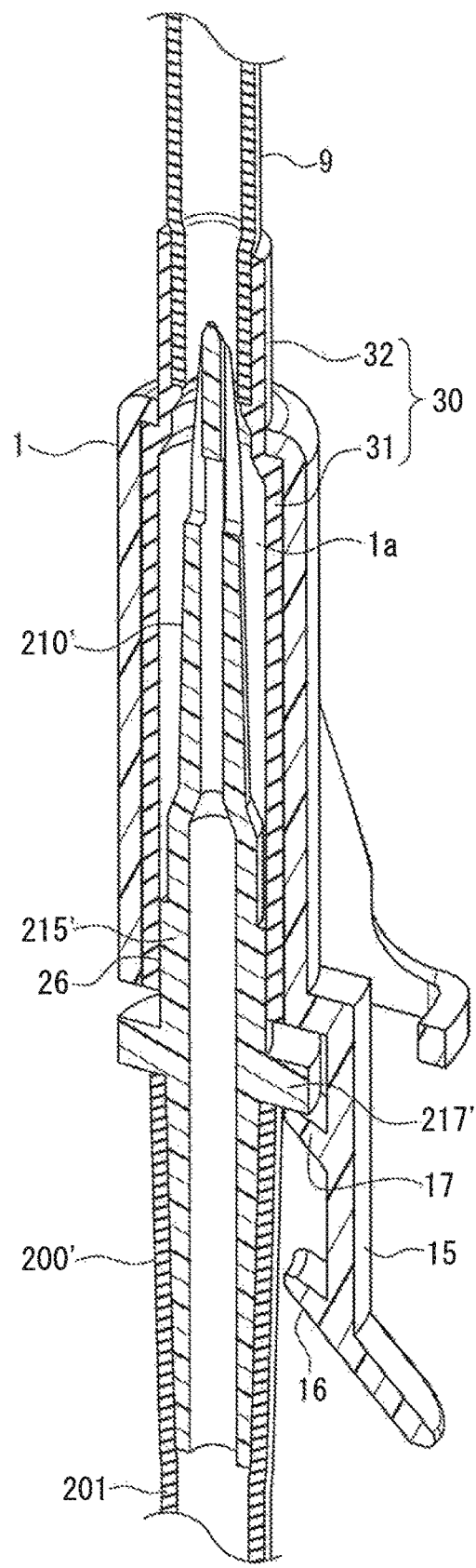
FIG. 13 is a cross-sectional perspective view showing a state in which the puncture needle connector according to the embodiment of the present invention is connected to a puncture needle of another infusion set.

FIG. 13 is an enlarged cross-sectional perspective view showing a state in which the connector 1 is connected to a puncture needle 210' of an infusion set 200' that is different from the above-described infusion set. In this infusion set 200', an intravenous cylinder is not integrated with the puncture needle 210'. The puncture needle 210' is inserted into the inner cavity 1a of the connector 1. A base portion 215' of the puncture needle 210' is inserted into the large tube portion 31 of the tubular member 30 of the connector 1, and a liquid-tight seal 26 is formed between the inner circumferential surface of the tubular member 30 (in particular, the large tube portion 31) and the outer circumferential surface of the base portion 215'. The position of an increased-diameter portion 217' relative to the puncture needle 210' and the base portion 215' shown in FIG. 13 is different from the position of the increased-diameter portion 217 relative to the puncture needle 210 and the base portion 215 shown in FIG. 10B. For this reason, in FIG. 13, the second claw 17 formed on the arm 15 of the connector 1 is engaged with the increased-diameter portion 217' provided integrally with the puncture needle 210'.

Different infusion sets may have different relative positional relationships of the puncture needle, the base portion, and the increased-diameter portion. Therefore, when the arm 15 is provided with a plurality of claws 16 and 17 as in the present embodiment, any one of the plurality of claws can be engaged with the increased-diameter portion. Thus, the number of types of puncture needles (infusion sets) that can be connected to the connector 1 increases.

Note that it is sufficient that the engagement structure (increased-diameter portion 217, 217') with which the claw of the connector 1 engages is provided integrally with the puncture needle. The phrase that the engagement structure is provided "integrally" with the puncture needle only requires that the position of the engagement structure relative to the puncture needle be unchanged. As long as this requirement is satisfied, the word "integrally" as used herein includes both the case where the engagement structure and the puncture needle are provided on a common one-piece component and the case where the engagement structure and the puncture needle are provided on separate components, and these separate components are combined with each other. The engagement structure is not limited to a protrusion that protrudes outward like the increased-diameter portions 217 and 217', and may also be a recess that is depressed from the outer circumferential surface. The engagement structure needs not be continuous in the circumferential direction.

It should be understood that the foregoing embodiments are given by way of example only. The present invention is not limited to the foregoing embodiments, and modifications can be made thereto as appropriate.

In the foregoing embodiments, a movement preventing means that prevents the tubular member 30 from moving upward relative to the outer cylinder 11 (connector main body 10) is constituted by the step 33 of the tubular member 30 and the small diameter portion 11a of the outer cylinder 11, which engage with each other in the vertical direction. However, the configuration of the movement preventing means is not limited to this configuration. For example, a flange-like portion (increased-diameter portion) protruding outward from the lower end (end on the first opening 21 side) of the tubular member 30 may be formed and engaged with the lower end 11b of the outer cylinder 11. The movement preventing means is not limited to an engagement structure in which the tubular member 30 and the outer cylinder 11 engage with each other, and may also be configured by fixedly attaching the tubular member 30 to the connector main body 10 (outer cylinder 11) through adhesive bonding, fusion bonding, or the like. Depending on the configuration of the movement preventing means, the tubular member 30 does not need the step 33, and the outer cylinder 11 does not need the small diameter portion 11a. The movement preventing means may also be configured so as to further prevent the tubular member 30 from moving downward relative to the connector main body 10.

In the foregoing embodiments, the tubular member 30 is inserted into the outer cylinder 11, and the small tube portion 32 of the tubular member 30 and the tube 9 are connected to each other. However, the present invention is not limited to this configuration.

For example, a configuration may be adopted in which the small tube portion 32 is omitted, and the lower end of the tube 9 is directly connected to the large tube portion 31. In this case, preferably, the large tube portion 31 and the tube 9 are connected to each other such that a step similar to the step 33 (see FIG. 3), which is formed in the case where the large tube portion 31 and the small tube portion 32 are connected to each other, is formed.

Alternatively, the tubular member 30 may be substituted with the tube 9. That is to say, a configuration may be adopted in which the tubular member 30 is omitted, and the tube 9 is extended into the outer cylinder 11 of the connector main body 10 to the lower end 11b of the outer cylinder 11. In this case, the portion of the tube 9 that extends in the outer cylinder 11 functions as a "flexible tubular member" in the same manner as the tubular member 30. The inner wall of the inner cavity 1a of the connector 1 is constituted by the inner circumferential surface of the tube 9 extending in the outer cylinder 11. When the puncture needle 210 is inserted into the inner cavity 1a of the connector 1, a liquid-tight seal is formed between the base portion 215 of the puncture needle 210 and the tube 9. Any movement preventing means, which has been described above, is provided on the tube 9 and the outer cylinder 11 so as to prevent the tube 9 from moving upward relative to the connector main body 10.

In the foregoing embodiments, when the puncture needle 210 is inserted into the inner cavity 1a of the connector 1, a liquid-tight seal is formed between the base portion 215 of the puncture needle 210 and the tubular member 30. However, the liquid-tight seal may also be formed using a configuration other than this configuration.

Figure 14:
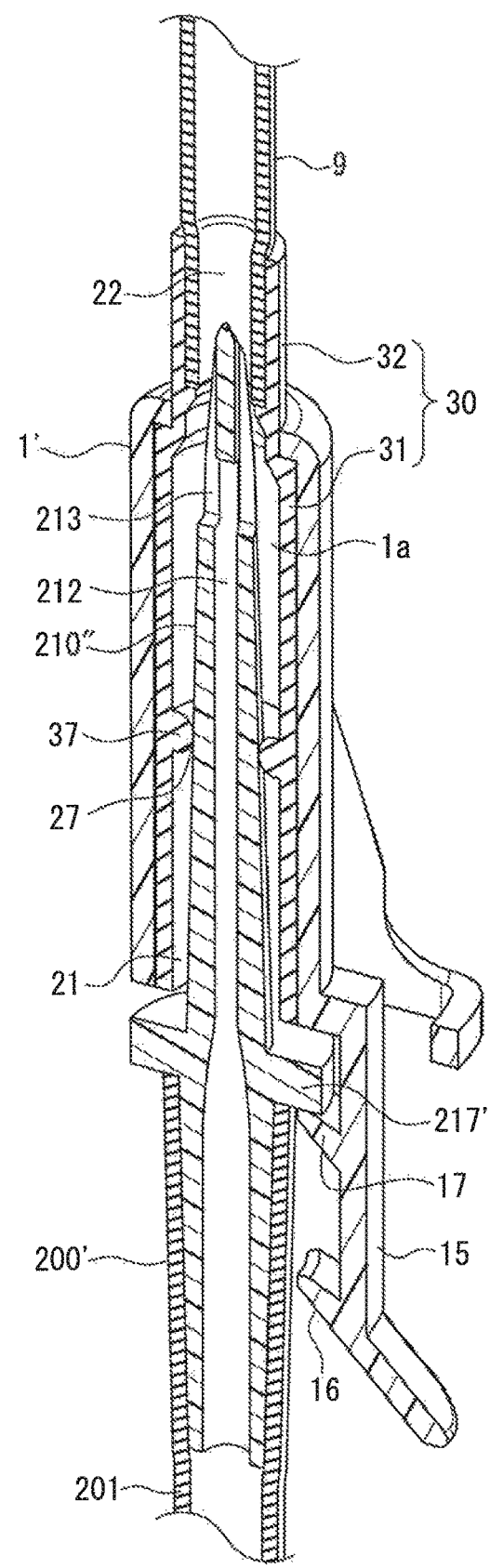
FIG. 14 is a cross-sectional perspective view showing a state in which a puncture needle connector according to another embodiment of the present invention is connected to a puncture needle of an infusion set.

FIG. 14 is a cross-sectional perspective view showing a state in which a connector 1' according to another embodiment of the present invention and a puncture needle 210" to each other. The connector 1' in FIG. 14 differs from the above-described connector 1 in that an annular projection 37 protruding into the inner cavity 1a is provided on the inner circumferential surface of the large tube portion 31 of the tubular member 30. The annular projection 37 is continuous in the circumferential direction and constitutes the inner circumferential surface of the inner cavity 1a together with the large tube portion 31. Moreover, the puncture needle 210" in FIG. 14 differs from the puncture needle 210' shown in FIG. 13 in that the base portion 215' with an increased diameter is not provided. As shown in FIG. 14, a liquid-tight seal 27 is formed between the outer circumferential surface of the puncture needle 210" inserted into the inner cavity 1a and the annular projection 37. The seal 27 is located nearer to the first opening 21 than the lateral hole 213, and thus, the flow channel 212 of the puncture needle 210" is in communication with the second opening 22 via the inner cavity 1a. The infusion in the inner cavity 1a is prevented from leaking to the outside through the first opening 21. In this manner, the connector of the present invention may also be provided with the annular projection 37 on the inner circumferential surface of the inner cavity 1a. In this case, the liquid-tight seal 27 can be formed between a portion on the outer circumferential surface of the puncture needle other than the base portion 215 or 215' and the inner circumferential surface (in particular, the annular projection 37) of the inner cavity 1a. Therefore, a liquid-tight seal can be formed between the puncture needle and the inner circumferential surface of the inner cavity 1a irrespective of the presence or absence of the increased-diameter portion and the external diameter of the increased-diameter portion.

The puncture needle 210 or 210' (see FIGS. 10B and 13) including the base portion 215 or 215' with an increased diameter may also be connected to the connector 1' shown in FIG. 14. In this case, the liquid-tight seal 27 is formed between the puncture needle 210 or 210' and the annular projection 37, and furthermore, the liquid-tight seal 25 or 26 (see FIGS. 10B and 13) is formed between the base portion 215 or 215' of the puncture needle 210 or 210' and the inner circumferential surface (portion other than the annular projection 37) of the inner cavity 1a. In this manner, in the connector of the present invention, a plurality of liquid-tight seals may be formed at different positions between the puncture needle and the inner circumferential surface of the inner cavity 1a.

Note that the annular projection 37 may also be provided at such a position that a liquid-tight seal can be formed between the annular projection 37 and the base portion 215 or 215' with an increased diameter, of the puncture needle.

Depending on the position in the vertical direction of the liquid-tight seal formed between the puncture needle and the inner circumferential surface of the inner cavity 1a of the connector, the large tube portion 31 needs not extend to the lower end 11b (see FIG. 4C) of the outer cylinder 11.

In FIG. 14, the annular projection 37 is provided integrally with the large tube portion 31 of the tubular member 30; however, the present invention is not limited to this configuration. For example, the annular projection 37 may be substituted with an O-ring. The O-ring is provided in such a manner that a liquid-tight seal can be formed between the O-ring and the outer circumferential surface of the puncture needle. The O-ring is held in the large tube portion 31 using any method. Alternatively, a configuration may be adopted in which the tubular member 30 is omitted, and the O-ring is fixed to the inner circumferential surface of the outer cylinder 11 using any method. In this case, the inner wall of the inner cavity 1a of the connector 1 is constituted by the inner circumferential surface of the outer cylinder 11. The tube 9 can be connected to the upper end of the outer cylinder 11 in a liquid-tight manner. In the case where the slits 13 are provided in the outer cylinder 11, it is necessary to dispose the O-ring at a higher position (second opening 22 side) than the slits 13 so as to prevent the infusion from leaking to the outside of the outer cylinder 11 through the slits 13.

The connector 1 may also be provided with a plurality of arms 15. Each arm 15 is provided with at least one claw that is engageable with the engagement structure provided integrally with the puncture needle. The plurality of arms 15 are preferably arranged equiangularly around the central axis 10a. The claw of each arm 15 can be engaged with the engagement structure provided integrally with the puncture needle 210. Since the plurality of claws engage with the engagement structure, the connector 1 and the puncture needle can be connected to each other with higher reliability. However, the need to bring the plurality of claws into engagement with the engagement structure may make the operation for connecting the connector 1 and the puncture needle to each other complicated.

The configuration of the male connector 5 is not limited to that in the foregoing embodiments. For example, as disclosed in Patent Documents 2 to 4, the male connector may have two lock levers, each including a lock claw that is engageable with the coinfusion port.

The male connector 5 may also include a flexible cover (see Patent Documents 6 and 7, for example) that cover the leading end of the male luer 51. When the male connector 5 is connected to the coinfusion port 150, the cover is compressed and deformed in the longitudinal direction of the male luer 51, and the male luer 51 penetrates the cover and further penetrates the septum 160.

The tube 9 that connects the connector 1 and the male connector 5 is not required to have flexibility, and may be made of a hard material (e.g., the same material as the connector main body 10 or the male connector 5) and have a degree of rigidity that substantially prevents the tube 9 from deforming. A configuration may also be adopted in which the tube 9, which is a separate member, is omitted, and, for example, the cylindrical portion 55 of the male connector 5 is directly connected to the second opening 22 (the upper end of the outer cylinder 11 or the small tube portion 32 in the foregoing embodiments) of the connector 1.

INDUSTRIAL APPLICABILITY

The present invention can be used in the field of medicine and specifically for infusion therapies. Above all, the present invention can be suitably used for an infusion therapy in which an infusion containing a hazardous drug is administered to a patient.

DESCRIPTION OF REFERENCE NUMERALS 1, 1' Connector (puncture needle connector)
1a Inner cavity of connector
2 Connecting tube
10 Connector main body
10a Central axis
11 Outer cylinder
11a Small diameter portion (movement preventing means)
14 Stopper
15 Arm
16, 17 Claw
16a, 17a Inclined surface of claw
21 First opening
22 Second opening
25, 26, 27 Liquid-tight seal
30 Tubular member
33 Step (movement preventing means)
5 Male connector
51 Male luer (male member)
62 Lock claw
9 Tube
150 Coinfusion port
210, 210', 210" Puncture needle
215, 215' Base portion of puncture needle
217, 217' Increased-diameter portion (engagement structure)

The invention claimed is:

1. A puncture needle connector that can be connected to a puncture needle having a sharp tip, the puncture needle connector comprising:
a hollow outer cylinder;
an arm provided at the hollow outer cylinder, the arm being elastically deformable by bending;
at least one claw provided on the arm; and
a flexible tubular member provided within the hollow outer cylinder, the flexible tubular member being a member different from the hollow outer cylinder,
wherein an inner cavity is formed within the flexible tubular member,
the inner cavity is in communication with an outside via a first opening and a second opening,
an inner wall of the inner cavity is constituted by the flexible tubular member,
the arm extends from the hollow outer cylinder, and
when the puncture needle is inserted into the inner cavity of the flexible tubular member via the first opening, the at least one claw engages with an engagement structure provided integrally with the puncture needle, an outer circumferential surface of the puncture needle and an inner circumferential surface of the flexible tubular member are in contact with each other in a radial direction, a liquid-tight seal is formed between the outer circumferential surface and the inner circumferential surface, and the puncture needle and the second opening are in communication with each other.

2. The puncture needle connector according to claim 1, further comprising
a movement preventing means that prevents the flexible tubular member from moving relative to the hollow outer cylinder in a direction in which the puncture needle is inserted into the inner cavity via the first opening.

3. The puncture needle connector according to claim 1, wherein the claw has an inclined surface, and
the inclined surface is inclined such that a distance from the inclined surface to a central axis of the puncture needle connector decreases in a direction in which the puncture needle is inserted into the inner cavity via the first opening.

4. The puncture needle connector according to claim 1, wherein the at least one claw comprises a plurality of claws on the arm spaced apart from one another along a longitudinal direction of the arm.

5. The puncture needle connector according to claim 1, further comprising
a stopper that limits an amount of bending deformation of the arm.

6. The puncture needle connector according to claim 1, wherein the inner cavity is in communication with the outside only via the first opening and the second opening.

7. A connecting tube comprising:
the puncture needle connector according to claim 1; and
a male connector,
wherein the male connector is in communication with the inner cavity via the second opening.

8. The connecting tube according to claim 7, wherein the male connector includes a male member to be inserted into a coinfusion port and a lock claw that is engageable with the coinfusion port.

9. The puncture needle connector according to claim 1, wherein the hollow outer cylinder is made of a material harder than the flexible tubular member.

10. The puncture needle connector according to claim 1, wherein the flexible tubular member is insertable into the hollow outer cylinder.

11. The puncture needle connector according to claim 1, wherein the hollow outer cylinder further comprises a pair of slits, wherein at least a portion of the arm at the hollow outer cylinder is defined by the pair of slits.

12. The puncture needle connector according to claim 1, wherein an inner wall of the hollow outer cylinder is engaged with an outer circumferential surface of the flexible tubular member.

* * * * *